US012746410B2

(12) United States Patent
Weber et al.

(10) Patent No.: US 12,746,410 B2
(45) Date of Patent: Sep. 29, 2026

(54) LIGHT APPLICATOR SYSTEM WITH PROTECTIVE SLEEVE

(71) Applicant: Richard Wolf GmbH, Knittlingen (DE)

(72) Inventors: Bernd Claus Weber, Karlsruhe (DE); Stephan Sieber, Knittlingen-Freudenstein (DE)

(73) Assignee: RICHARD WOLF GMBH, Knittlingen (DE)

( * ) Notice: Subject to any disclaimer, the term of this patent is extended or adjusted under 35 U.S.C. 154(b) by 385 days.

(21) Appl. No.: 18/559,871

(22) PCT Filed: May 10, 2022

(86) PCT No.: PCT/DE2022/200097
§ 371 (c)(1),
(2) Date: Nov. 9, 2023

(87) PCT Pub. No.: WO2022/237943
PCT Pub. Date: Nov. 17, 2022

(65) Prior Publication Data
US 2025/0073492 A1 Mar. 6, 2025

(30) Foreign Application Priority Data
May 14, 2021 (DE) ..................... 10 2021 204 908.7

(51) Int. Cl.
*A61N 5/06* (2006.01)

(52) U.S. Cl.
CPC .................................... *A61N 5/062* (2013.01)

(58) Field of Classification Search
CPC ... A61N 5/06; A61N 2005/0612; A61B 18/20
See application file for complete search history.

(56) References Cited

U.S. PATENT DOCUMENTS 6,048,359 A * 4/2000 Biel .................... A61N 5/0601 606/2
6,371,954 B1 * 4/2002 Lee ....................... A61H 39/06 606/189

(Continued)

FOREIGN PATENT DOCUMENTS

DE 68929404 T2 12/2002
DE 102019212197 A1 2/2021
DE 102019129556 A1 5/2021

*Primary Examiner* — Lynsey C Eiseman
(74) *Attorney, Agent, or Firm* — McGlew and Tuttle, P.C.

(57) ABSTRACT

A light applicator system (31), for examination and/or treatment of an organic body (5), includes a light applicator (21) having a distal-side insertion portion (1) with a light emitting element (7) at the distal end for piercing tissue (3) and a needle tip (9) at least partially distally of the light-emitting element and tapering distalwards. A positioning element (33) is fixable in a position and orientation relative to the organic body and has a receptacle (35) for the light applicator providing an orientation. The light applicator (21) has a movable protective sleeve (39) with an axial position that protectively surrounding the needle tip and an axial position based on the position of the insertion portion relative to the positioning element that is pushed back relative to the insertion portion proximalwards from the needle tip. The protective sleeve serves as an insertion sleeve into the receptacle of the positioning element.

15 Claims, 27 Drawing Sheets

(56) References Cited

U.S. PATENT DOCUMENTS

| | | | | |
|---|---|---|---|---|
| 2003/0130575 | A1* | 7/2003 | Desai ............... | A61B 17/00234<br>600/417 |
| 2007/0112343 | A1* | 5/2007 | Mische .................. | A61B 18/20<br>606/41 |
| 2021/0016102 | A1 | 1/2021 | Mamiya | |

* cited by examiner

LIGHT APPLICATOR SYSTEM WITH PROTECTIVE SLEEVE

CROSS REFERENCE TO RELATED APPLICATIONS

This application is a United States National Phase Application of International Application PCT/DE2022/200097, filed May 10, 2022, and claims the benefit of priority under 35 U.S.C. § 119 of German Application 10 2021 204 908.7, filed May 14, 2021, the entire contents of which are incorporated herein by reference.

TECHNICAL FIELD

The present disclosure relates to a light applicator system for examination and/or treatment of an organic body, in particular for photodynamic therapy (PDT) of pathological tissue.

BACKGROUND

It is known to use endoscopes to make video recordings of the inside of a human or animal body for the purpose of medical diagnosis and/or therapy. It is a constant endeavor here to make the insertion portion of endoscopes as thin as possible so that the smallest possible cavities can be viewed and the tissue is only minimally affected.

However, endoscopes are not only used to take pictures or make video recordings, but are also used as diagnostic or therapeutic tools themselves. For example, fluorescence endoscopy can be used for the detection and localization of pre-malignant and early malignant tissue; this does not require a natural true-color representation of the tissue, but only fluorescence excitation, which can be used to distinguish pathological tissue from healthy tissue. The pathological tissue itself or an accumulation of bacteria indicating pathological tissue can be specifically fluoresced by means of light radiation and thus can be recognizably localized compared to the surrounding healthy tissue. Fluorescence endoscopy can be carried out, for example, as part of photodynamic diagnosis (PDD) and/or photodynamic therapy (PDT) using a photosensitizer or marker substance that selectively accumulates on pathological tissue.

In photodynamic therapy (PDT), light is applied directly to or even into pathological tissue by means of a light applicator in order to promote the light-induced formation of oxygen radicals by means of the locally enriched photosensitizer or marker substance and thereby destroy the pathological tissue, such as a tumor. Typically, laser light is coupled into a light guide and directed to the tissue. If the pathological tissue is located on an outer surface, e.g. the skin, or an inner surface, e.g. the inner surface of the esophagus or intestinal wall, then the therapy light can be coupled out relatively easily and beamed onto the pathological tissue surface. However, if the pathological tissue extends over a volume, it is not always possible to effectively irradiate a tumor from "outside" due to the limited penetration depth of the light into the tissue. In this case, PDT is particularly effective if the light is emitted as isotropically as possible from inside the pathological tissue volume. For this purpose, the light applicator must be pierced into the pathological tissue. This is also called interstitial PDT (through internal surfaces) and/or percutaneous PDT (through the skin).

For example, U.S. Pat. No. 6,048,359 describes how multiple light applicators are inserted into pathological tissue using a positioning grid.

The disadvantage of the known solution is that the very sharp applicator tip is, on the one hand, dangerously sharp for a user and, on the other hand, can easily break off during handling before the actual piercing into the patient's skin.

This results in the task of providing a light applicator in which the sharp and sensitive applicator tip is protected until the point of actual piercing, in such a way that it does not endanger the user and does not break off before the actual piercing into the patient's skin.

SUMMARY

According to the present disclosure, a light applicator system for examination and/or treatment of an organic body is provided for solving this problem, wherein the light applicator system comprises at least one light applicator and a positioning element, wherein the light applicator comprises a distal-side insertion portion with at least one actively light-emitting element, e.g. an LED at the distal end for piercing into tissue of the organic body, wherein the insertion portion has a needle tip which is arranged at least partially distally from the at least one actively light-emitting element and tapers to a point distalwards, wherein the needle tip can be designed as a light-transparent scattering body for scattering light emitted in the distal direction, wherein the positioning element can be fixed at least temporarily in a defined position and orientation with respect to the organic body and has at least one receptacle for the at least one light applicator, in which the at least one light applicator has, at least temporarily, a defined orientation relative to the organic body, wherein the light applicator has a protective sleeve which is axially movable relative to the insertion portion, which in a first axial position relative to the insertion portion protectively encloses the needle tip, and in a second axial position determined by an axial position of the insertion portion (1) relative to the positioning element is pushed back proximalwards from the needle tip relative to the insertion portion, wherein the protective sleeve serves as an insertion sleeve for safe insertion into the at least one receptacle of the positioning element.

In the case of the light applicator disclosed here, therefore, no laser light guide is used, but rather the diagnostic or therapeutic light is generated in situ at the distal end of the light applicator by an actively light-emitting element, e.g. a miniaturized LED, e.g. with a lateral width of less than 1 mm, with "actively" meaning that the light-emitting element absorbs electrical energy and converts it into light, i.e. does not just pass it onwards in the form of a light guide. An expensive laser is therefore not needed, and so costs are greatly reduced. The light applicator disclosed herein, or at least its insertion portion, can be manufactured very cheaply and can thus be realized as a sterile disposable article for single use, making costly cleaning and sterilization by the user obsolete. In the case of larger tumors or entire pathological organs or organ areas, the light applicator system can have a plurality of light applicators that are used simultaneously for PDT by piercing the organ with them in a manner distributed over the entire organ in order to homogeneously illuminate the entire organ. Since the photosensitizer or marker substance selectively accumulates only in pathological tissue and reacts there under the influence of light, healthy tissue is not damaged by the light. On the one hand, the pathological tissue then no longer needs to be localized so precisely beforehand and on the other hand, the risk of pathological tissue remaining unnoticed and untreated is reduced.

For percutaneous PDT with multiple light applicators, it may be useful for the positioning element to have a plurality of receptacles and to form an organ-specific template that can be placed and/or adhered in a defined manner on or to the patient's skin in order to indicate to a user insertion sites, angles and/or depths for the light applicators and to achieve the most complete and largely homogeneous illumination of the organ.

However, the light applicator can be used not only for therapy, but also for examination, i.e. diagnosis. Especially in combination with an endoscope or with the light applicator as part of an endoscope, the fluorescence produced by the light applicator of a photosensitizer or marker substance enriched in pathological tissue can be observed.

Optionally, the protective sleeve can have, at least in portions, an outer diameter that fits precisely into an inner diameter of the at least one receptacle of the positioning element. This only allows an exactly coaxial orientation of the protective sleeve in the at least one receptacle of the positioning element and prevents any pivoting. Once the protective sleeve is in the at least one receptacle of the positioning element, only axial movement of the light applicator is possible. The protective sleeve is preferably pushed distalwards into the at least one receptacle of the positioning element until the protective sleeve reaches an axial desired position, which is preferably a maximum distal position of the protective sleeve. For example, when the protective sleeve is pushed distally into the at least one receptacle of the positioning element, it can strike against the positioning element with a stop when the desired position is reached.

Optionally, the outer diameter of the protective sleeve may taper distalwards at the distal end and/or the inner diameter of the at least one receptacle of the positioning element may widen proximalwards at the proximal end. This facilitates the insertion of the protective sleeve into the receptacle of the positioning element.

Optionally, the insertion portion of the light applicator can be rigid and have a greater length in the axial direction than the protective sleeve. The insertion portion preferably corresponds to a rigid needle that is as thin as possible, at the light-diffusing tip of which there is arranged the light of a miniaturized LED arranged in or at the tip.

Optionally, the protective sleeve can be captively secured to the insertion portion of the light applicator. In this way, the protective sleeve also protects the needle tip beyond the actual application, for example during transport and/or disposal of the light applicator.

Optionally, the light applicator can have a handle element on the proximal side for manual positioning of the light applicator. As long as the orientation is not yet fixed by the inserted protective sleeve in the positioning element, the handle element can also be used to orient the light applicator outside the positioning element. The handle element can be fixedly connected to the insertion portion or can be detachably coupled thereto. The handle element may be reusable if necessary and the detachable insertion portion may be provided as a single-use disposable article.

Optionally, when the light applicator is inserted distally into the at least one receptacle of the positioning element, the protective sleeve can be secured in the first axial position until the protective sleeve reaches a desired position in the positioning element in the at least one receptacle of the positioning element at which the insertion portion can be pushed distalwards out of the protective sleeve. Preferably, the desired position is a maximum distal position of the protective sleeve in the receptacle of the positioning element. In the desired position, the protective sleeve is preferably completely or at least largely within the receptacle of the positioning element and is engaged therein.

Optionally, when the light applicator is pulled out proximally from the at least one receptacle of the positioning element, the protective sleeve can be secured in the desired position in the positioning element until the protective sleeve assumes the first axial position with respect to the insertion portion, in which the protective sleeve can be pulled out proximalwards from the at least one receptacle of the positioning element.

Optionally, the light applicator system may further comprise an elastically deformable and/or movable engagement element, wherein the engagement element is arranged between the insertion portion and the protective sleeve such that it elastically yields or moves upon overcoming an axial force to such an extent that the protective sleeve can reach the first axial position distalwards and/or leave it proximalwards. Optionally, the first engagement element can be part of the protective sleeve and/or the insertion portion.

Optionally, the light applicator system may comprise a further elastically deformable and/or movable engagement element, wherein the second engagement element is arranged between the protective sleeve and the at least one receptacle of the positioning element in such a way that, when the second axial force is overcome, it elastically yields or moves to such an extent that the protective sleeve can reach the desired position in the positioning element distalwards and/or leave it proximalwards. Optionally, the second engagement element can be part of the protective sleeve or the positioning element.

Optionally, distalwards the first axial force may be greater than the second axial force and proximalwards the second axial force may be greater than the first axial force.

The terms "distally" and "proximally" are intended herein to mean a relative position that is distal or proximal, respectively, to a user of the system as a reference position. The terms "distal-side" and "proximal-side" are herein intended to mean, respectively, positions on a distal and proximal side of an object. The terms "distalwards" and "proximalwards" are intended herein to mean directions extending in a distal sense and proximal sense, respectively.

The disclosure is explained in greater detail below with reference to exemplary embodiments shown in the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1B:
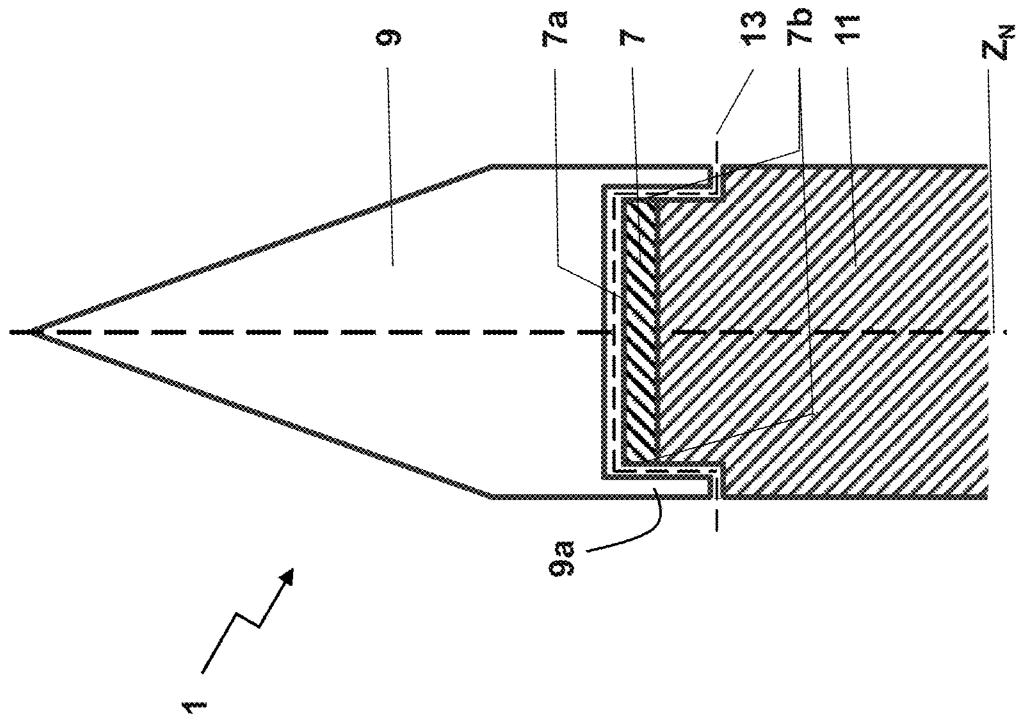
FIG. 1*a*, and FIG. 1*b* are two schematic longitudinal sectional views of exemplary embodiments of a needle tip of an insertion portion of a light applicator system disclosed herein.
Figure 1A:
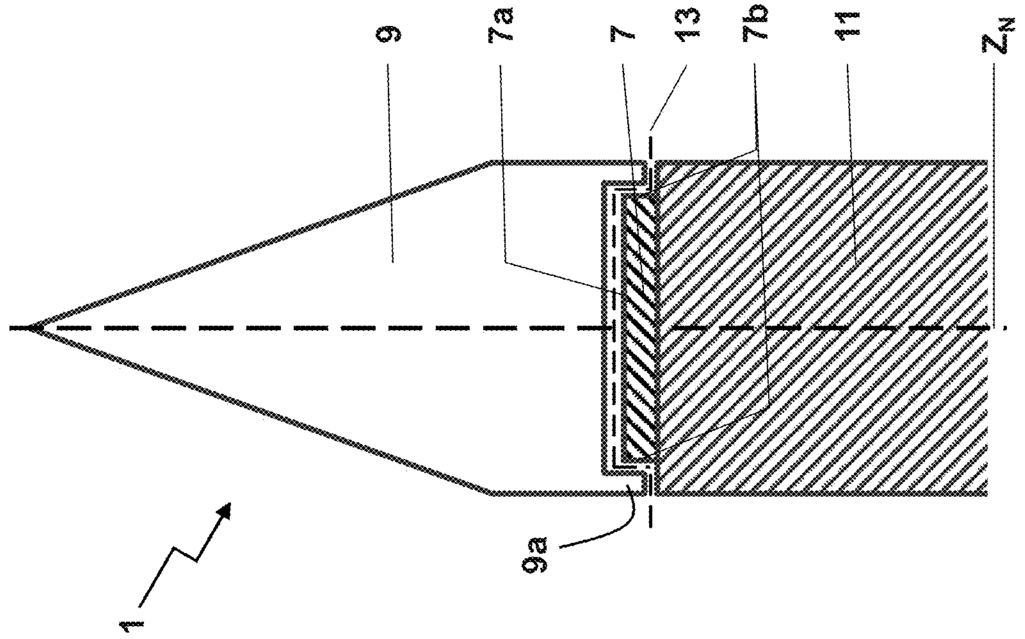

Referring to the drawings, FIGS. 1*a*, 1*b*, 2, 3*a* and 3*b* illustrate the problem solved with the light applicator system disclosed herein. FIGS. 1*a* and 1*b* show various embodiments of a distal end of an insertion portion 1 of a light applicator of a light applicator system disclosed herein. The distal end is for piercing tissue 3 of an organic body 5 (see FIGS. 3*a* and 3*b*) to irradiate the tissue 3 with light for photodynamic therapy (PDT) or diagnosis (PDD). The insertion portion 1 of the light applicator is designed to be needle-shaped, as thin as possible (with a diameter of less than 2 mm, for example) and rigid for the most minimally invasive treatment or diagnosis possible.

The distal end of the insertion portion 1 here has, by way of example, an actively light-emitting element 7 in the form of an LED, the main radiation direction of which is directed in the longitudinal direction $Z_N$ of the insertion portion 1. At least partially distally of the LED 7 is a needle tip 9 tapering distalwards, which has a light-transparent scattering body for scattering the light of the LED 7. The needle tip 9 is formed here substantially in one piece from the light-transparent scattering body, which may, for example, comprise plastic with one or more reinforcement elements.

The LED 7 is arranged on a distal end face of a conductor element 11. The conductor element 11 is designed here as a solid metal rod. The conductor element 11 can serve both as an electrical conductor for supplying power to the LED 7 and as a heat conductor for dissipating heat generated by the LED 7 proximally. For this purpose, a core of the conductor element 11 may comprise, for example, copper, which is a good conductor of heat and electricity. To stiffen the conductive element 11, which may have a diameter of 1 mm or less, a sheath of the conductive element 11 may be formed of a material that is more resistant to bending, such as steel. When the core and cladding of the conductive element 11 are electrically insulated from each other, for example by a thin insulating layer between them, the core and cladding can act as a forward and return pair for supplying power to the LED 7.

As shown in FIGS. 1*a* and 1*b*, the cross-sectional area of the conductor element 11 is only slightly larger than the cross-sectional area of the LED 7. In order, on the one hand, not to attach the needle tip 9 exclusively to an end face 7*a* of the LED 7 and, on the other hand, not to extend with the needle tip 9 beyond the cross-sectional area of the conductor element 11, the needle tip 9 has a proximal-side sleeve-shaped portion 9*a* which embraces the LED 7 circumferentially and connects the needle tip 9 directly to the end face of the conductor element 11. The needle tip 9 is connected to the LED 7 and the conductor element 11 via a planar connection point 13, preferably by means of an integral bond along the connection point 13. To enlarge the planar connection point 13 directly between the needle tip 9 and the conductor element 11, in the embodiment shown in FIG. 1*b*, the proximal-side sleeve-shaped portion 9*a* is axially longer and the conductor element 11 has a correspondingly tapered distal portion which is embraced circumferentially by the sleeve-shaped portion 9*a* of the needle tip 9. This allows the needle tip 9 to be bonded directly to the conductor element 11 not only at the end face, but also circumferentially at the tapered distal portion of the conductor element 11. This makes the connection point 13 larger and stronger.

Figure 2:
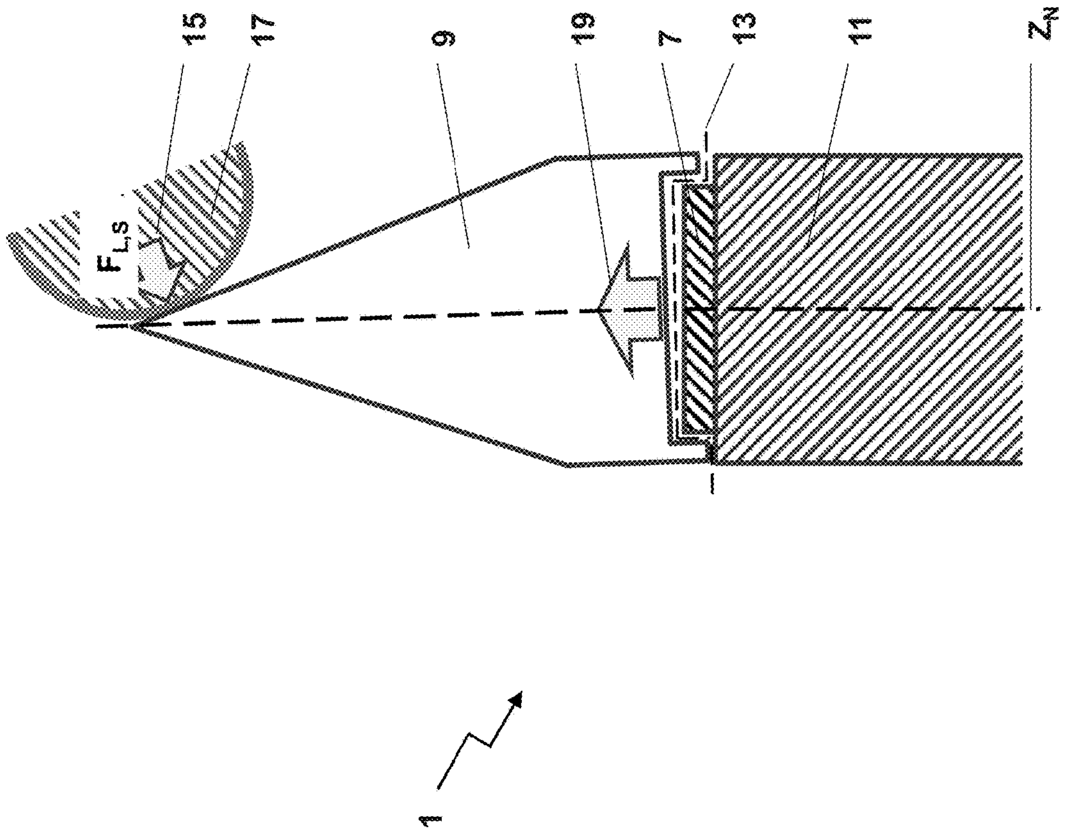
FIG. 2 is a schematic longitudinal sectional view of the exemplary embodiment of a needle tip of an insertion portion shown in FIG. 1*a* under lateral force application.

FIG. 2 shows, specifically, that the needle tip 9 can easily snap or break off. Since the needle tip 9 must be as pointed as possible for minimally invasive treatment or therapy, it is preferably much longer in the longitudinal direction $Z_N$ than its diameter. If a lateral force $F_{L,S}$ 15 is now exerted by an external body 17 on the distal needle tip end of the needle tip 9, an increased detachment force 19 acts by leverage on the connection point 13, which can then break as shown. This danger also exists for the embodiment according to FIG. 1*b*, although the connection point 13 is in principle stronger there. However, in both embodiments according to FIGS. 1*a* and 1*b*, there is a risk that the proximal-side sleeve-shaped portion 9*a* can break off from the rest of the needle tip 9, as the sleeve-shaped portion 9*a* can only be made very thin.

FIGS. 1*a*, 1*b* and 2 show an exemplary embodiment in which the actively light-emitting element is a single LED 7 arranged on the distal end face of the conductor element 11. Alternatively to the single LED 7, several actively light-emitting elements can also be used and these can also be other actively light-emitting elements, e.g. laser diodes. As an alternative to being placed on the distal end face of the conductor element 11, the at least one actively light-emitting element can also be placed on the lateral surface of the distal insertion portion 1 or of the conductor element 11 of the light applicator 21. In addition, the needle tip 9 need not necessarily be a separate part that is bonded to the distal end of the insertion portion 1. Instead, the needle tip 9 may also be a continuation of the conductor element 11. In that case, the fundamental object is to protect the user and the patient from accidental contact with the pointed needle tip 9 and a possible resulting injury. In the following embodiments, the LED 7 arranged at the distal end face of the conductor element 11 with the needle tip 9, which is designed as a scattering body, applied, for example glued, on the distal side, is considered to be an example.

Figure 3B:
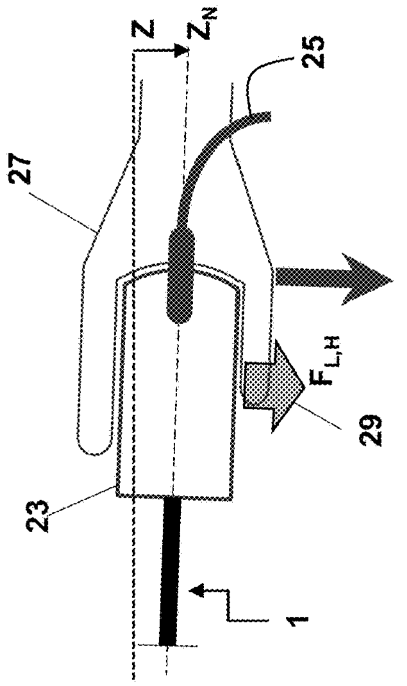
FIG. 3*a* and FIG. 3*b* are two schematic longitudinal sectional views to explain how a lateral force is applied when using a light applicator system disclosed herein.
Figure 3A:
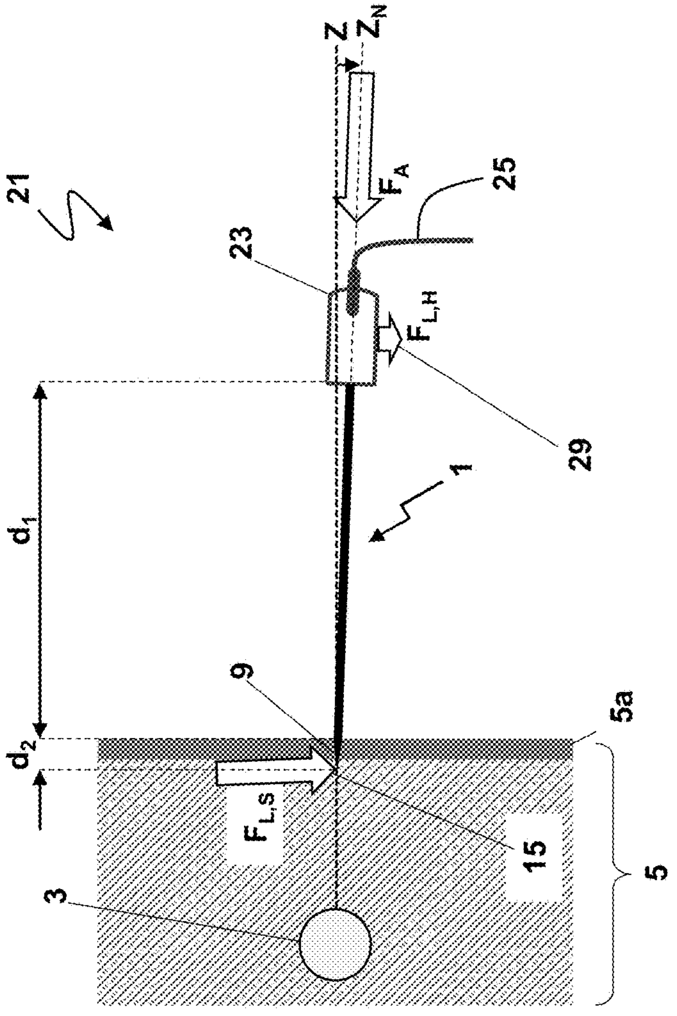

FIGS. 3*a* and 3*b* show how a lateral force $F_{L,S}$ 15 can be applied to the needle tip 9 using a light applicator system 21 disclosed herein. The light applicator system has a light applicator 21 which comprises the insertion portion 1, a handle element 23 and a power supply unit (not shown) which can be connected via a connecting cable 25.

An operator grips the handle element 23 with their hand 27 in order to pierce the insertion portion 1 through the skin 5*a* into the patient's body 5 in the direction of the tissue 3 to be examined or treated. FIGS. 3*a* and 3*b* schematically indicate the proportions, which cannot be shown here to scale. In this case, the insertion portion 1 has a relatively large length $d_1+d_2$ from the distal end of the needle tip 9 to the handle element 23, e.g. 20 cm or more, and is very thin, e.g. with a diameter of 1 mm or less. The length of the needle tip 9 is denoted here by $d_2$ and the remainder of the length of the insertion portion 1 is denoted by $d_1$, wherein $d_1>>d_2$. Due to these proportions, the lever principle results in a relatively large lateral force $F_{L,S}$ 15 acting on the needle tip 9 when the operator exerts only a relatively small lateral force $F_{L,H}$ 29 on the handle element 23. In the case shown, the skin 5*a* was first pierced vertically in the Z-direction, but then the light applicator 21 was slightly angled by a relatively small lateral manual force $F_{L,H}$ 29 on the handle element 23, which is unavoidable with manual handling. A much greater lateral force $F_{L,S}$ 15 then acts on the needle tip 9, which can lead to the needle tip 9 snapping or being broken off, as $$F_{L,S} \approx \frac{d_1}{d_2} \cdot F_{L,H}$$

applies.

Figure 4:
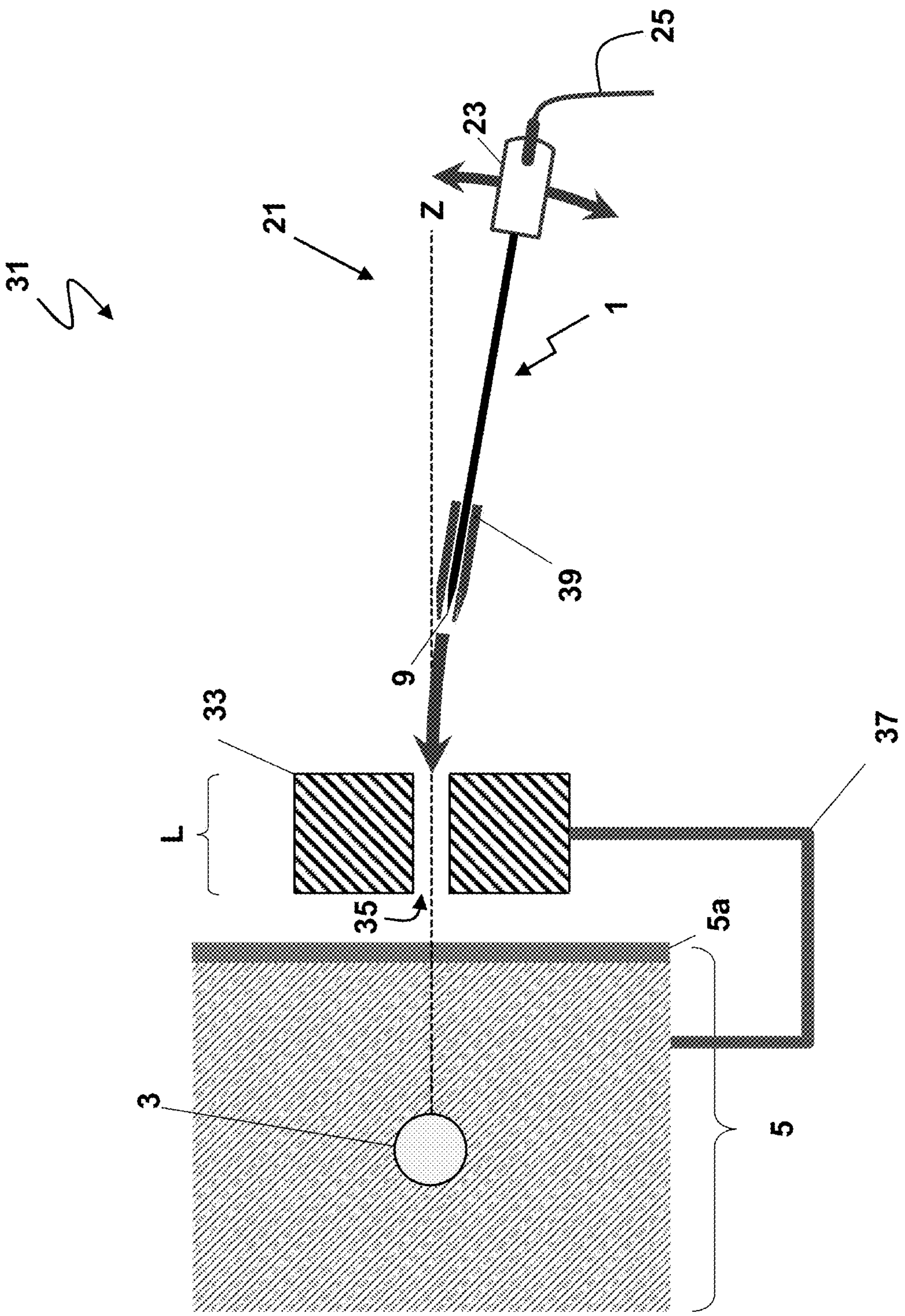
FIG. 4 is a schematic longitudinal sectional view of an exemplary embodiment of a light applicator system disclosed herein prior to insertion of the light applicator into the positioning element.

FIG. 4 shows a light applicator system 31 in which the risk of the needle tip 9 snapping or breaking off is significantly reduced. The light applicator system 31 has a light applicator 21 with an insertion portion 1, a needle tip 9 at the distal end and a handle element 23 at the proximal end. In addition, the light applicator system 31 comprises a positioning element 33 which is at least temporarily fixable in a defined position and orientation relative to the organic body 5. The positioning element 33 can be spaced from the skin 5*a*, as shown schematically in FIG. 4, or can be arranged directly in contact with the skin 5*a*, for example adhered to the skin 5*a*. The positioning element 33 can be a template with at least one receptacle 35 for the light applicator 21. The receptacle 35 can be a recess or a hole in the positioning element 33 defining the piercing site on the skin 5*a* in a plane orthogonal to the perpendicular piercing direction Z. Preferably, a plurality of receptacles 35 are arranged in this plane orthogonal to the perpendicular piercing direction Z to allow the operator to select from a predefined set of piercing sites and/or to use a plurality of light applicators 21 simultaneously. The positioning element 33 and the patient's body 5 are preferably fixed or fixable relative to each other by means of a fixing element 37, preferably both with respect to a fixed local reference body, for example a treatment table.

In the axial piercing direction Z, the positioning element 33 has a certain thickness L, so that the receptacle 35 has a length L in the axial direction Z. Through this length L, the positioning element 33 defines not only the position of the piercing site, but also the orientation of the light applicator 21 with respect to the body 5. In the case shown in FIG. 4, only perpendicular piercing into the skin 5*a* is permitted through the receptacle 35. The positioning element 33 is preferably rigid and inflexible for this purpose.

Since the risk of the needle tip 9 being snapped or broken off under canting (see FIG. 4) during manual insertion of the insertion portion 1 into the rigid and inflexible positioning element 33 is even greater than with canted insertion directly into the skin 5*a* without positioning element 33 as shown in FIGS. 3*a* and 3*b*, the light applicator system 31 has a protective sleeve 39. The protective sleeve 39 is axially movable relative to the insertion portion 1, but is temporarily fixed in at least a first axial position relative to the insertion portion 1. In the first axial position relative to the insertion portion 1 shown in FIG. 4, the protective sleeve 39 encloses the needle tip 9 protectively. In the first axial position shown, the protective sleeve 39 projects axially beyond the distal end of the needle tip 9. This protects not only the needle tip 9, but also a patient and/or an operator from accidentally piercing with the very pointed needle tip 9. The protective sleeve 39 is here captively secured to the insertion portion 1 of the light applicator 21 in such a way that it cannot fall off or be pulled off distalwards from the insertion portion 1. The first axial position shown in FIG. 4 is the maximum distal axial position relative to the insertion portion 1 of the light applicator 21. In the proximal direction, the handle element 23 or another stop (not shown here) can limit the maximum axial freedom of movement of the protective sleeve 39 along the insertion portion 1.

An inner diameter of the receptacle 35 is adapted so as to precisely fit an outer diameter of the protective sleeve 39, so that the latter can be inserted into the receptacle 35 of the positioning element 33 with a precise fit in the axial direction Z. To facilitate insertion into the receptacle 35, the outer diameter of the protective sleeve 39 is tapered distalwards at the distal end of the protective sleeve 39.

Figure 5:
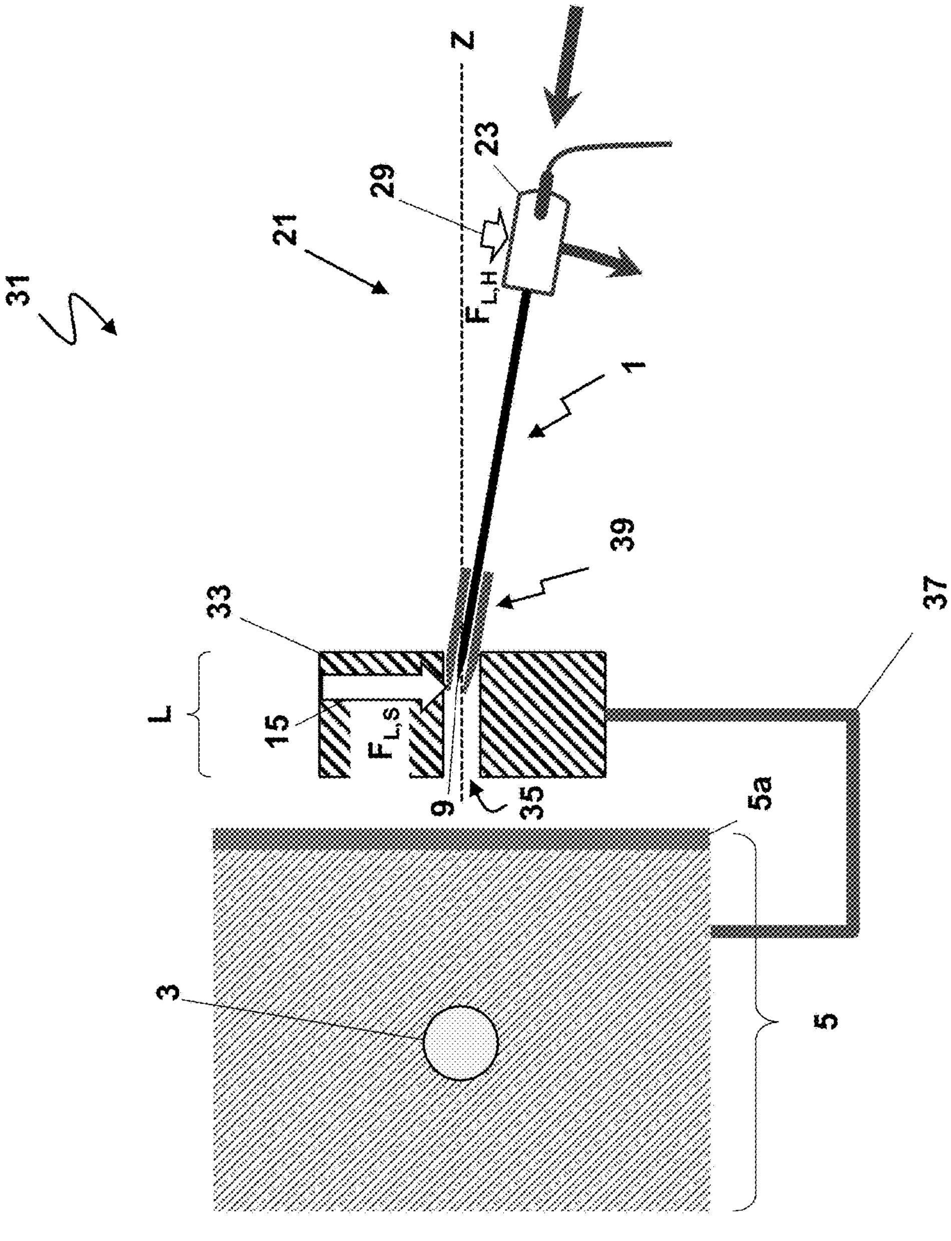
FIG. 5 is a schematic longitudinal sectional view of an exemplary embodiment of a light applicator system disclosed herein when tilted during insertion of the light applicator into the positioning element.

FIG. 5 shows how the protective sleeve 39 protects the needle tip 9 from the effect of the large lateral force $F_{L,S}$ 15, which is already caused by a relatively small manual canting force $F_{L,H}$ 29 on the handle element 23. The axial length of the protective sleeve 39 exceeds the axial length of the needle tip 9 by at least double, in this case by a multiple. The axial length of the protective sleeve 39 corresponds to at least half the length L of the receptacle 35; here they are substantially the same.

Figure 6:
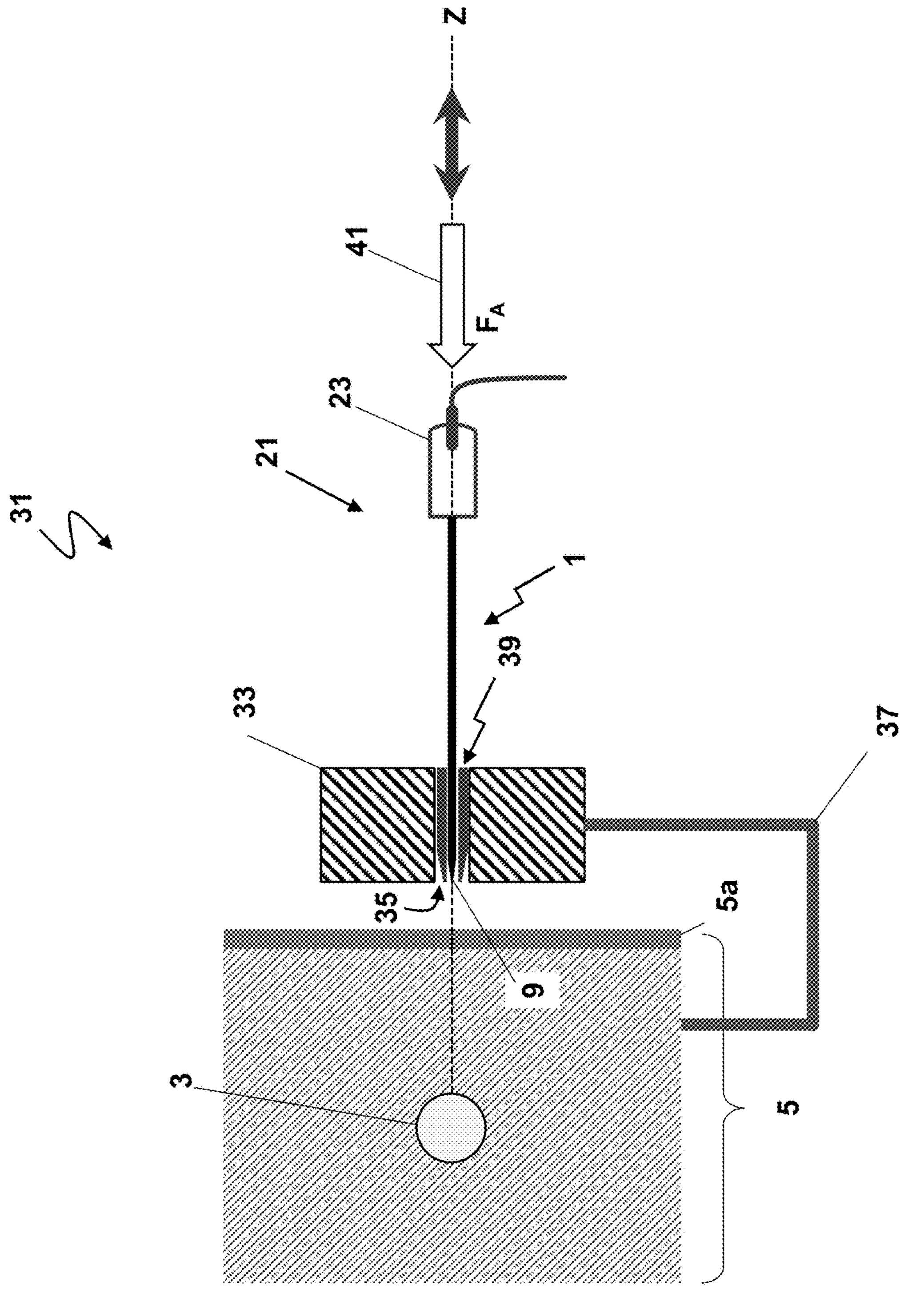
FIG. 6 is a schematic longitudinal sectional view of an exemplary embodiment of a light applicator system disclosed herein upon insertion of the light applicator into the positioning element with the protective sleeve in the first axial position with respect to the insertion portion.

In FIG. 6, the insertion portion 1 is inserted together with the protective sleeve 39 into the receptacle 35 of the positioning element 33 so that the light applicator 21 is oriented exactly perpendicular to the skin 5*a* in the Z-direction. The protective sleeve 39 is still in the first axial position relative to the insertion portion 1, in which it protectively encloses the needle tip 9. For further advancing of the insertion portion 1, the operator only has to manually exert an axial force $F_A$ on the handle element 23. Any manual canting forces $F_{L,H}$ 29 on the handle element 23 would only cause a bending of the insertion portion 1, but no more than lateral force $F_{L,S}$ 15 on the needle tip 9 protected by the protective sleeve 39.

Figure 7:
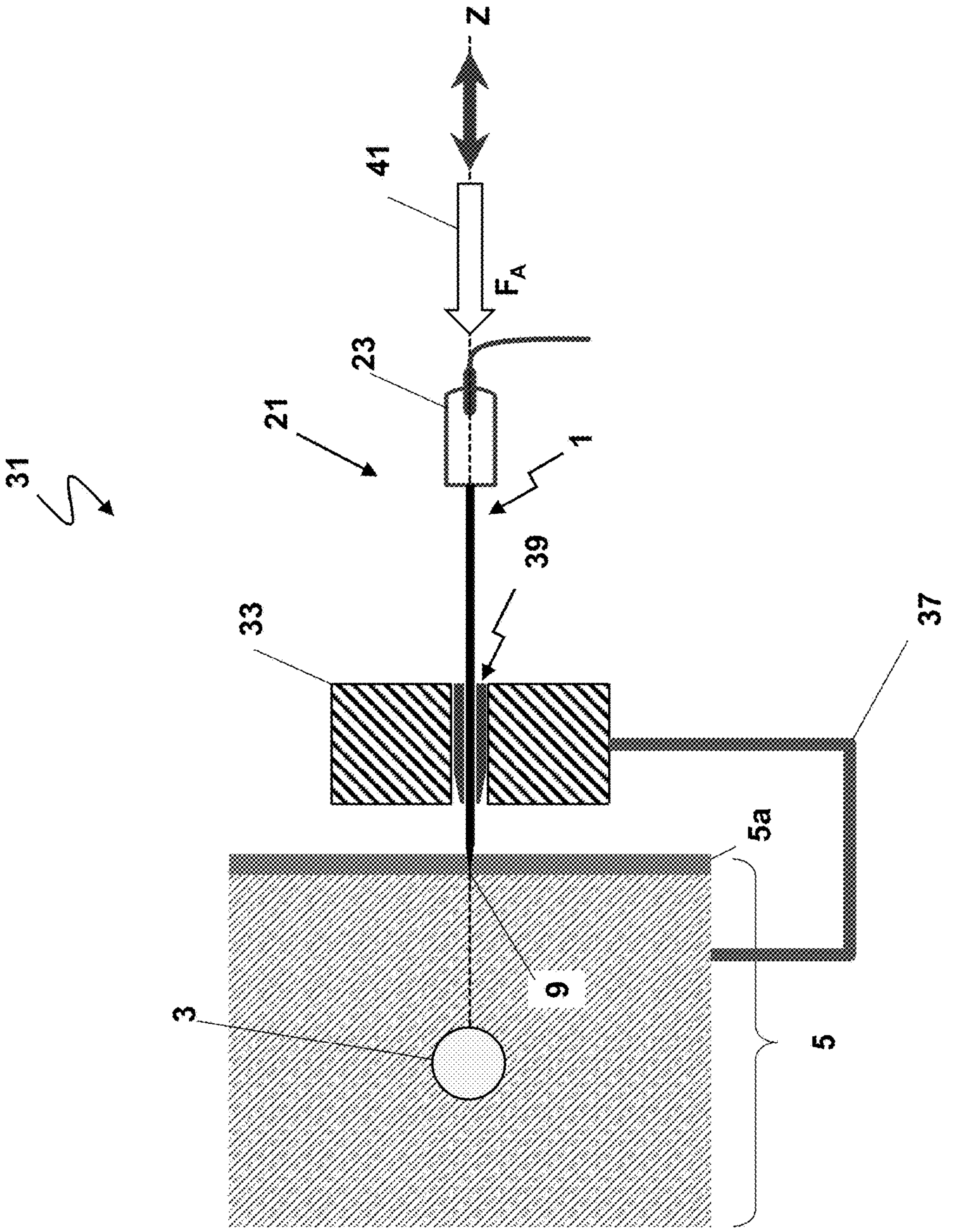
FIG. 7 is a schematic longitudinal sectional view of an exemplary embodiment of a light applicator system disclosed herein during piercing of the insertion portion into the body.

In FIG. 7, the needle tip 9 of the insertion portion 1 has already pierced the skin 5*a*. However, the protective sleeve 39 has remained in the position shown in FIG. 6 in the receptacle 35 of the positioning element 33. The protective sleeve 39 can, for example, have a stop (not shown in FIG. 7) which defines a maximum distal position of the protective sleeve 39 in the receptacle 35 of the positioning element 33 by the stop striking against the positioning element 33. By pushing the insertion portion 1 distally out of the protective sleeve 39, the protective sleeve 39 has left the first axial position with respect to the insertion portion 1 and is now in a second axial position in which the protective sleeve 39 is axially retracted with respect to the needle tip 9. There can be many second axial positions, wherein the second axial position depends on the penetration depth of the needle tip 9 into the body 5, the maximum of which is limited only by the length of the insertion portion 1, i.e. would be reached if the handle element 23 were to abut the positioning element 33.

Figure 8:
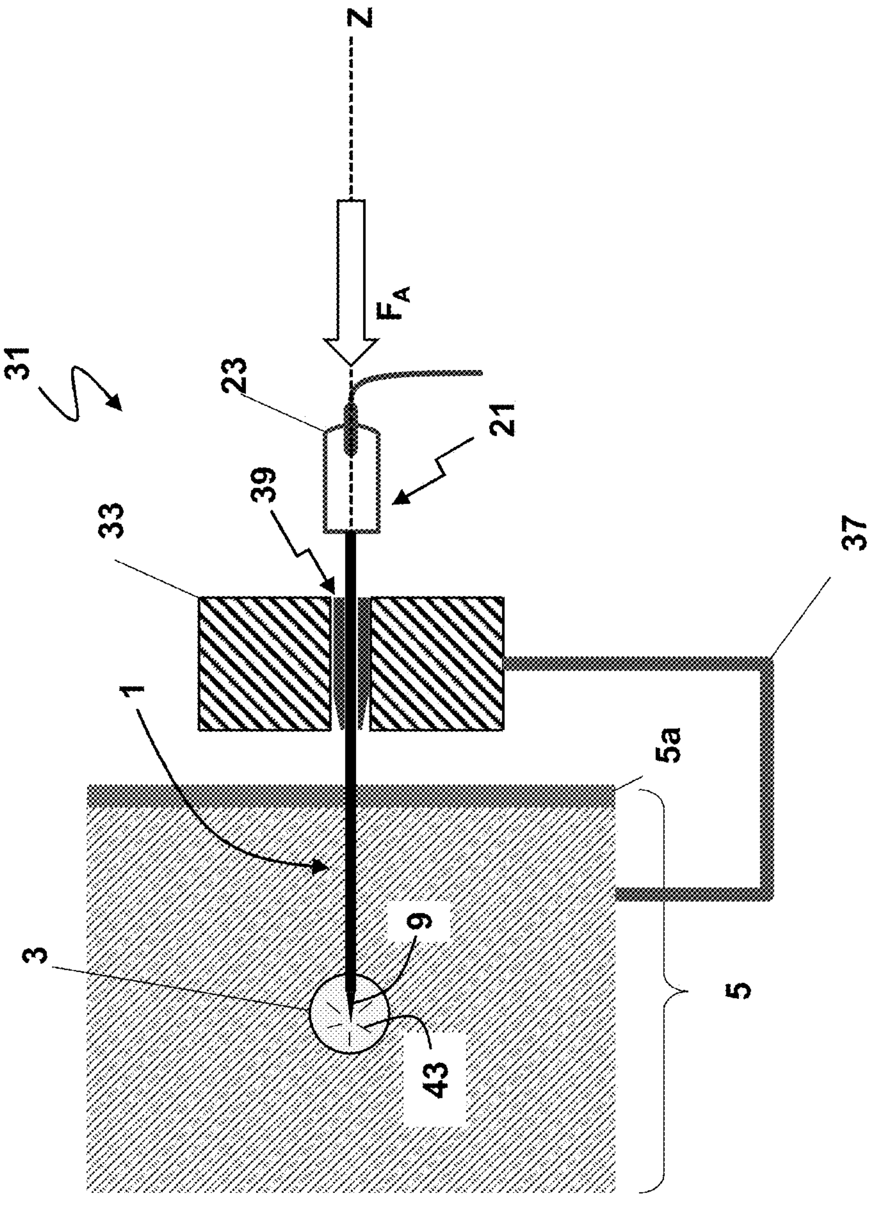
FIG. 8 is a schematic longitudinal sectional view of an exemplary embodiment of a light applicator system disclosed herein during piercing of the insertion portion through the body and during piercing into the tissue to be examined/treated.

In FIG. 8, the needle tip 9 has pierced into the tissue 3 and has reached the axial target position in which the PDD or PDT can be performed, i.e. the LED 7 is switched on and the needle tip 9 with the light-transparent scattering body scatters the light 43 of the LED 7 into the tissue 3 in a solid angle that is as large as possible, preferably of significantly more than $3\pi$. The tissue 3 can be, for example, a tumor or other pathological tissue which reacts to the light 43 of the LED 7 with or without the aid of a photosensitizer enriched there, wherein locally limited toxic substances, e.g. oxygen radicals, are produced which damage the pathological tissue 3. Since this process requires a certain irradiation time of the light, the insertion portion 1 is preferably fixed relative to the positioning element 33 in this selected second axial position. For this purpose, for example, a clamping element not shown here can clamp the protective sleeve 39 to the insertion portion 1. In addition, the clamping element can also clamp the protective sleeve 39 to the positioning element 33.

Figure 9:
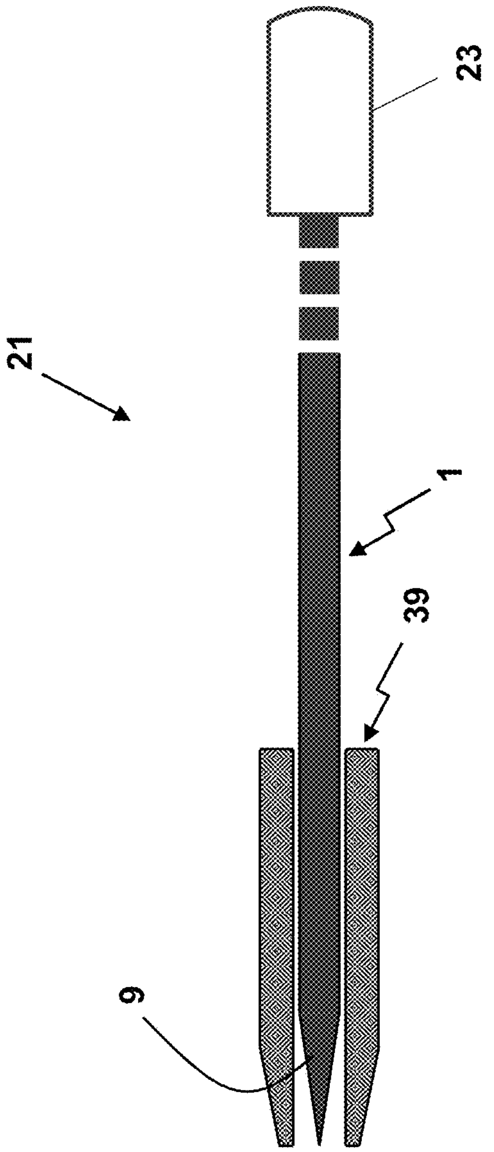
FIG. 9 is a schematic longitudinal sectional view of an exemplary embodiment of the light applicator of a light applicator system disclosed herein.

FIG. 9 shows the light applicator 21 schematically enlarged, wherein its length would not have fitted on the paper if it had been enlarged to scale and is therefore shown shortened in length. The protective sleeve 39 has an inner diameter that fits exactly on the outer diameter of the insertion portion 1. The protective sleeve 39 protectively encloses the needle tip 9 in the first axial position shown relative to the insertion portion 1. The handle element 23 is located at the proximal end of the light applicator 21. At the distal end of the protective sleeve 39, it is chamfered on the outside, i.e. the outer diameter tapers distalwards, so that the protective sleeve can be inserted more easily into the receptacle 35 of the positioning element 33.

Figure 10:
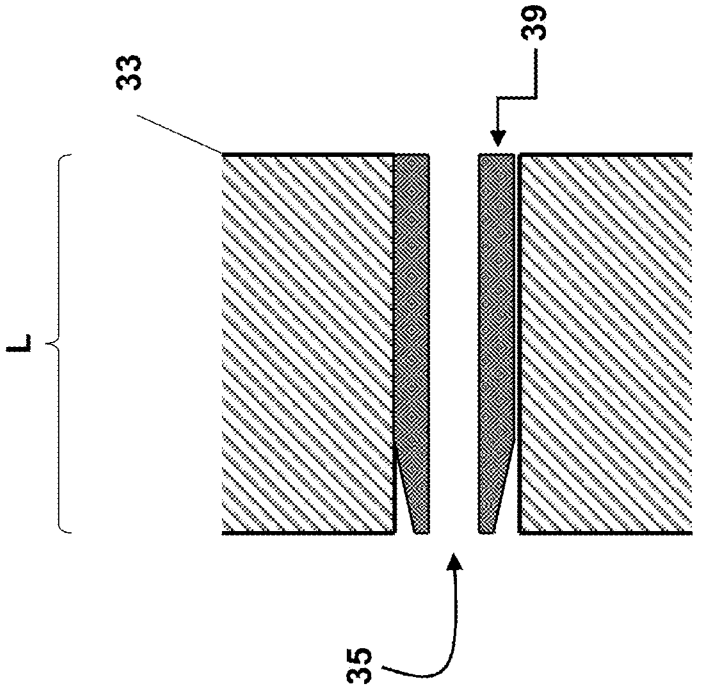
FIG. 10 is a schematic longitudinal sectional view of an exemplary embodiment of the protective sleeve in the positioning element of a light applicator system disclosed herein, wherein the light applicator is not shown.

In FIG. 10, the protective sleeve 39 is shown in the receptacle 35 of the positioning element 33, in which it sits with an accurate fit. Here, the length of the protective sleeve 39 is substantially equal to the thickness L of the positioning element, which corresponds to the axial length L of the receptacle 35, thus achieving good guidance.

Figure 11:
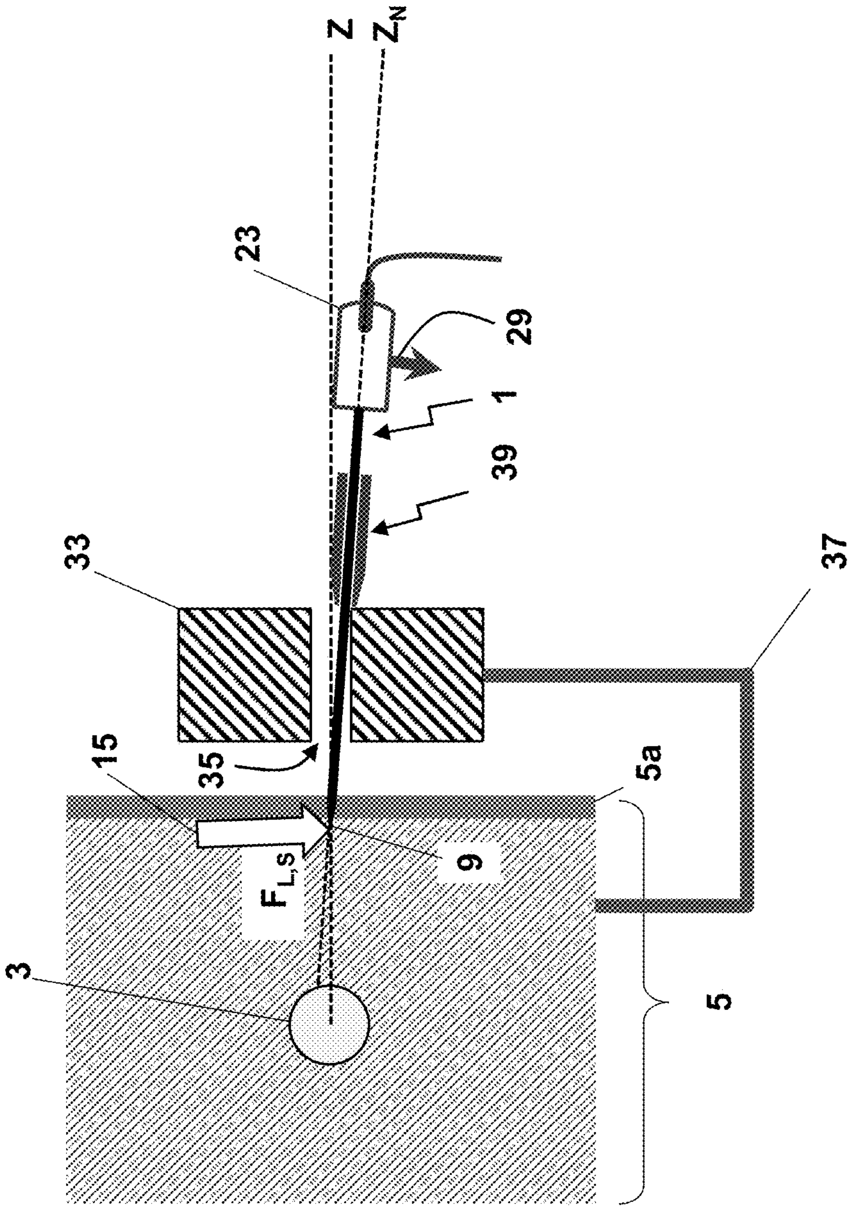
FIG. 11 is a schematic longitudinal sectional view of an exemplary embodiment of a light applicator system disclosed herein during piercing of the insertion portion into the body, wherein the protective sleeve is not seated in the first axial position with respect to the insertion portion.

FIG. 11 shows a problem when the protective sleeve 39 is not correctly seated in the receptacle 35 of the positioning element 33 and at the same time has left the first axial position. This can happen, for example, during insertion when the distal end of the protective sleeve 39 bumps against the positioning element 33 and the needle tip 9 is pushed distalwards out of the protective sleeve 39. Similarly, this situation can arise during retraction of the light applicator 21 proximally if the protective sleeve 39 is prematurely pulled proximalwards out of the receptacle 35 of the positioning element 33 before the needle tip 9 has been pulled far enough into the protective sleeve 39 for the protective sleeve 39 to occupy the protective first axial position. Since the inner diameter of the receptacle 35 is matched to the outer diameter of the protective sleeve 39, which is larger than the outer diameter of the insertion element 1, the insertion element 1 will have significant lateral play in the receptacle 35 without the correctly positioned protective sleeve 39. As shown in FIG. 11, the light applicator 21 may then be tilted so that the longitudinal axis $Z_N$ is no longer aligned with the intended insertion direction Z. As a result, considerable lateral forces $F_{L,S}$ 15 may act on the needle tip 9 as described above, which can lead to the needle tip 9 being snapped off or breaking off.

Figure 12:
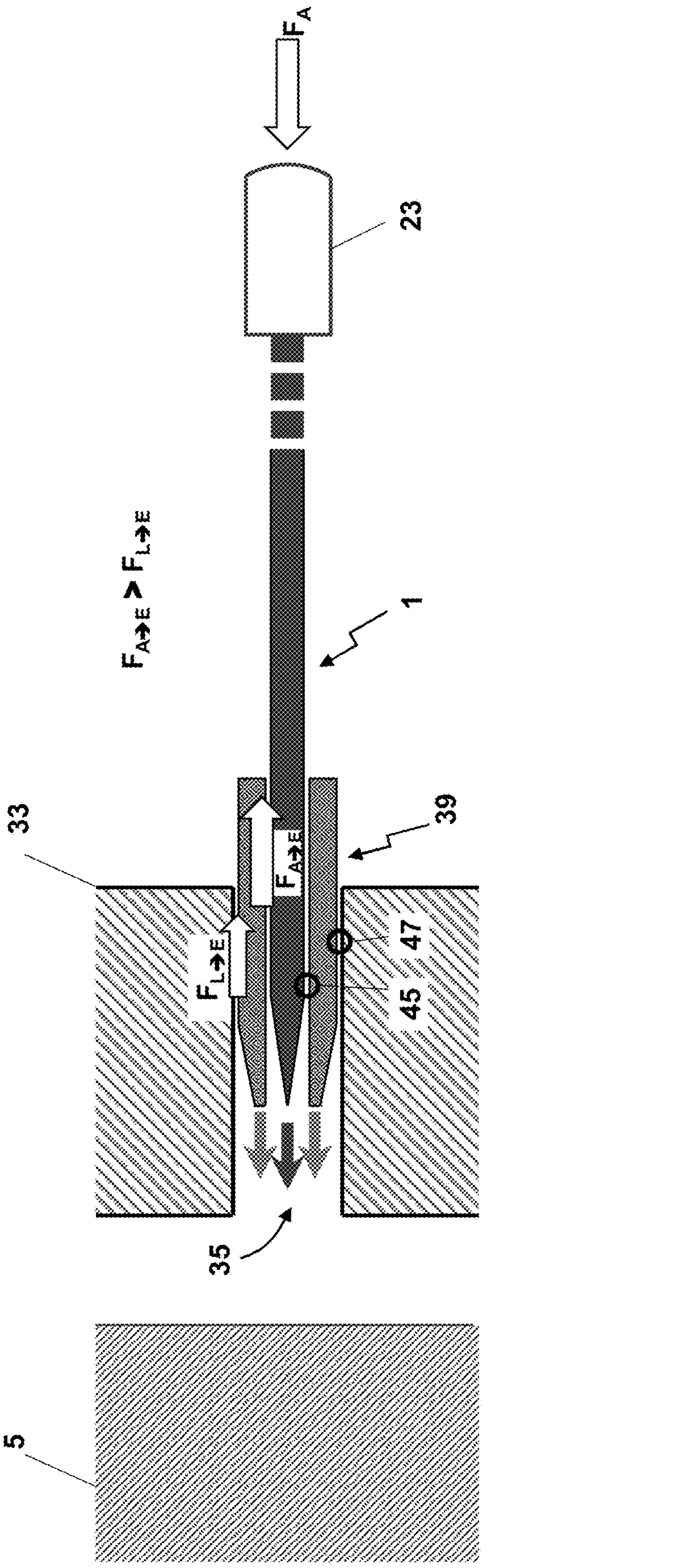
FIG. 12 is a schematic longitudinal sectional view of an exemplary embodiment of the light applicator during insertion into the positioning element with the protective sleeve in the first axial position with respect to the insertion portion and before the protective sleeve has reached an axial desired position in the positioning element.

FIGS. 12 to 17 illustrate the axial force conditions that preferably prevail in the light applicator system 31 disclosed herein. When the protective sleeve 39 is inserted into the receptacle 35 as shown in FIG. 12, the protective sleeve 39 remains in the first axial position. To achieve this, the protective sleeve 39 has, on the inside, a first mechanical interface 45 with the insertion portion 1, and, on the outside, a second mechanical interface 47 with the positioning element 33. The interfaces 45, 47 can be, for example, friction surfaces or friction points. The interfaces 45, 47 each generate a resistance force opposite to the axial insertion force $F_A$, for example an adhesive and/or sliding friction force. As long as the protective sleeve 39 has not yet reached the final maximum distal position in the receptacle 35, the resistance force $F_{L\rightarrow E}$ generated by the second interface 47 is smaller than the piercing force $F_A$. The resistance force $F_{A \to E}$ generated by the first interface 45 is, however, greater than the resistance force $F_{L \to E}$ generated by the second interface 47. Therefore, the protective sleeve 39 remains in the first axial position with respect to the insertion portion 1 and transmits the insertion force $F_A$ to the protective sleeve 39 by means of the resistance force. $F_{A \to E}$. Therefore, the protective sleeve 39 moves distalwards into the receptacle 35 against the smaller resistance force $F_{L \to E}$.

Figure 13:
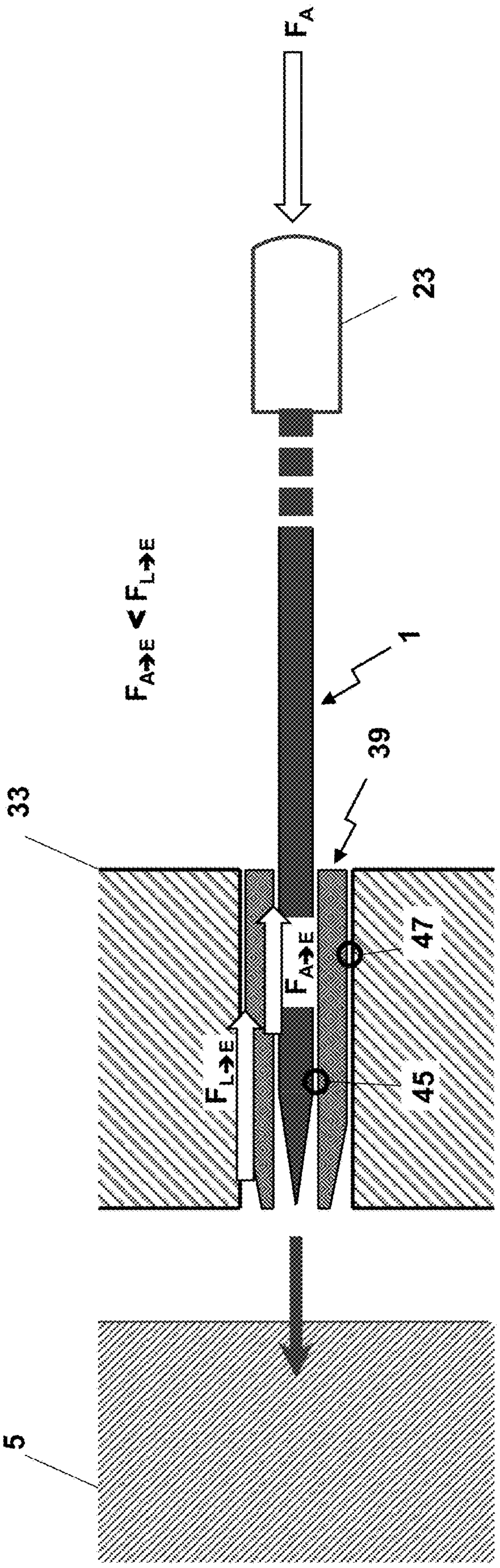
FIG. 13 is a schematic longitudinal sectional view of an exemplary embodiment of the light applicator during insertion into the positioning element with the protective sleeve in the first axial position with respect to the insertion portion, wherein the protective sleeve has just reached the axial desired position in the positioning element.

FIG. 13 shows the moment at which the protective sleeve 39 has reached the final distal position, i.e. the desired position, in the receptacle 35, and at the same time is still in the first axial position with respect to the insertion portion 1. The protective sleeve 39 may, for example, have just abutted against the positioning element 33 with a stop (not shown). The stop could be understood as part of the second interface 47, wherein, upon contact, the proximal resistance force $F_{L \to E}$ immediately increases to such an extent that it becomes greater than the proximal-side resistance force $F_{A \to E}$. Thus, the protective sleeve 39 cannot be pushed further distally as the positioning element 33 is fixed relative to the body 5. The operator must increase the piercing force $F_A$ compared to FIG. 12 in order to overcome the greater resistance force $F_{A \to E}$ of the first interface 45 to push the needle tip 9 distalwards out of the protective sleeve 39.

Figure 14:
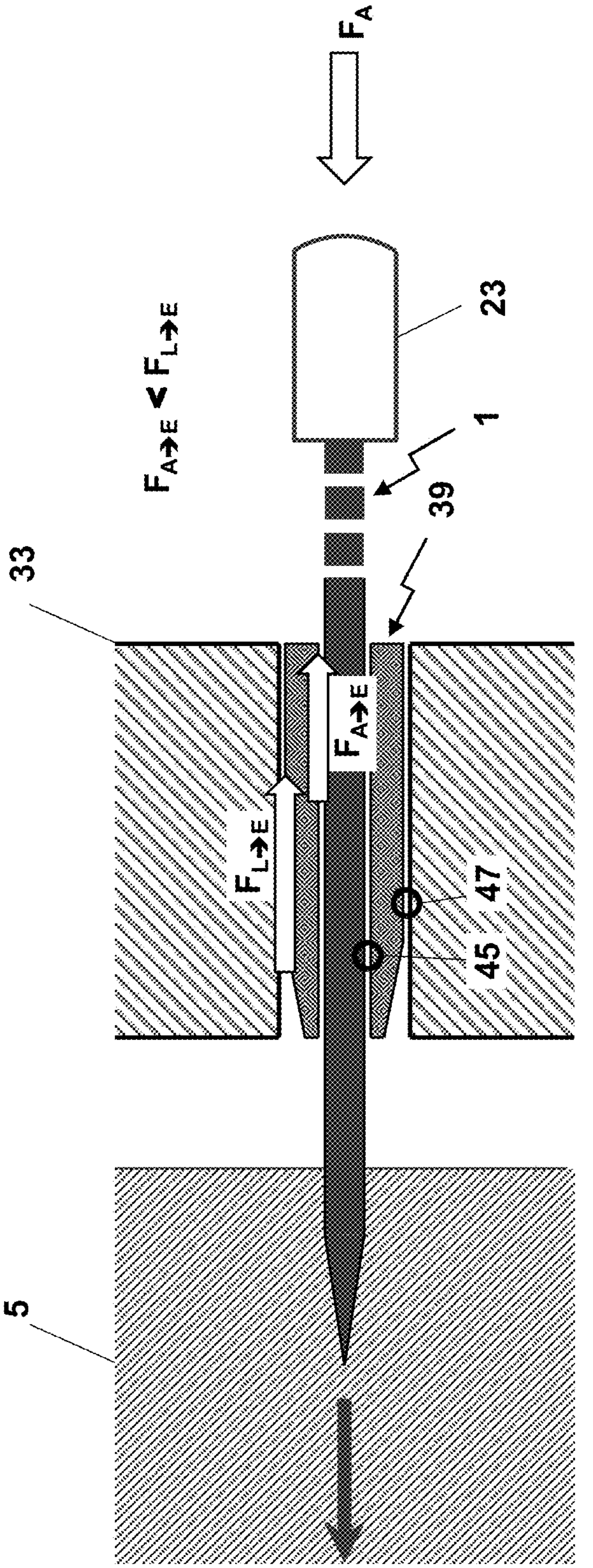
FIG. 14 is a schematic longitudinal sectional view of an exemplary embodiment of the light applicator when the needle tip of the insertion portion is pushed distally out of the protective sleeve located in the axial desired position in the positioning element into the body.

In FIG. 14, the protective sleeve 39 has left the first axial position by pushing the insertion portion 1 distalwards out of the protective sleeve 39 which is in the maximum distal position, i.e. the desired position. As soon as an initially high resistance force $F_{A \to E}$ in the first axial position of the first interface 45 in the first axial position is overcome, the resistance force $F_{A \to E}$ outside the first axial position can be lower, so that, during further advancing, as shown in FIG. 14, the piercing force $F_A$ can be lower again. For example, the initially high resistance force can be $F_{A \to E}$ can include a static friction force and/or an elastic deformation force. The resistance force $F_{A \to E}$ can then become lower when the static frictional force changes to a lower dynamic frictional force and/or an elastic deformation force is no longer required. During and after the piercing in the skin 5*a* and the body 5, additional resistance forces counteract the piercing force $F_A$, which must be correspondingly large so that the needle tip 9 can be inserted as far as the tissue 3. However, in order to make the piercing as minimally invasive as possible, the insertion portion 1 is made as thin as possible within the limits of stability and the needle tip 9 is made as pointed as possible so that the resistance forces induced by the skin 5*a* and/or the body 5 are minimal to the greatest possible extent.

Figure 15:
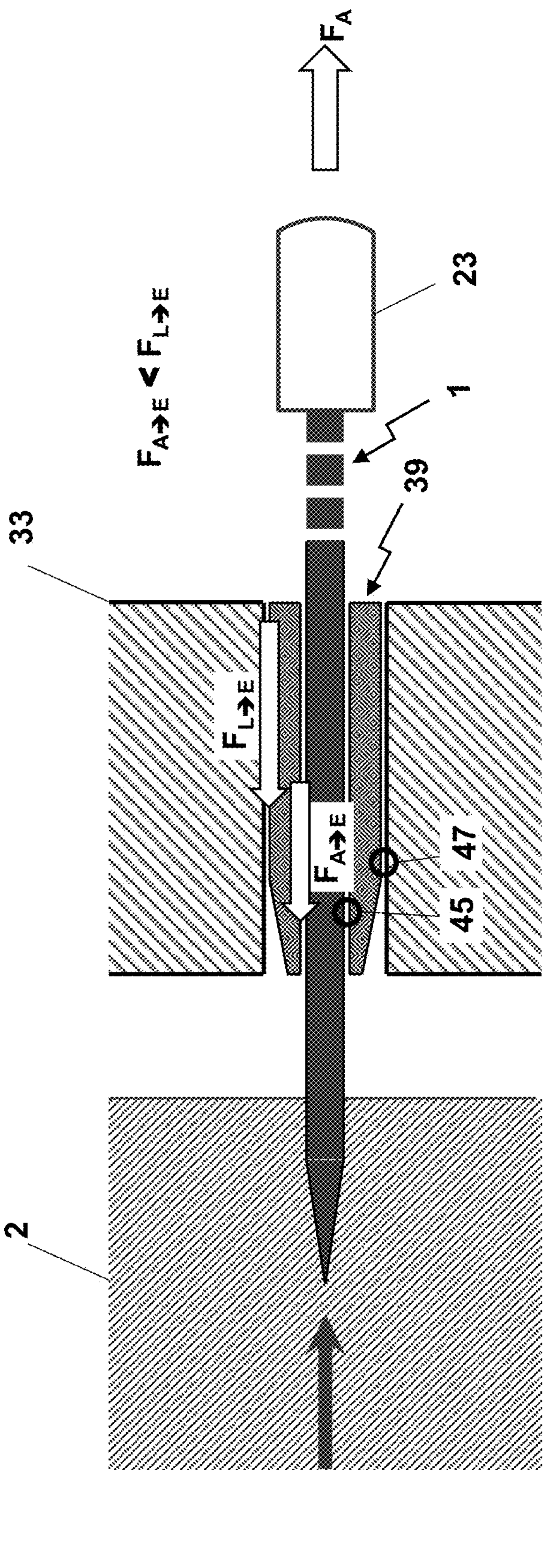
FIG. 15 is a schematic longitudinal sectional view of an exemplary embodiment of the light applicator when the needle tip of the insertion portion is pulled proximally out of the body into the protective sleeve located in the axial desired position in the positioning element.

In FIG. 15, the insertion portion 1 is retracted proximally from the body 5 after PDD or PDT has been performed. Here, the protective sleeve 39 is engaged in the maximum distal position, so that the distalward resistance force $F_{L \to E}$ generated by the second interface 47 is higher than the distalward resistance force $F_{A \to E}$ generated by the first interface 45. As a result, the protective sleeve 39 remains in the maximum distal position, i.e. desired position, in the receptacle 35 of the positioning element 33 while the needle tip 9 is retracted proximally into the protective sleeve 39.

Figure 16:
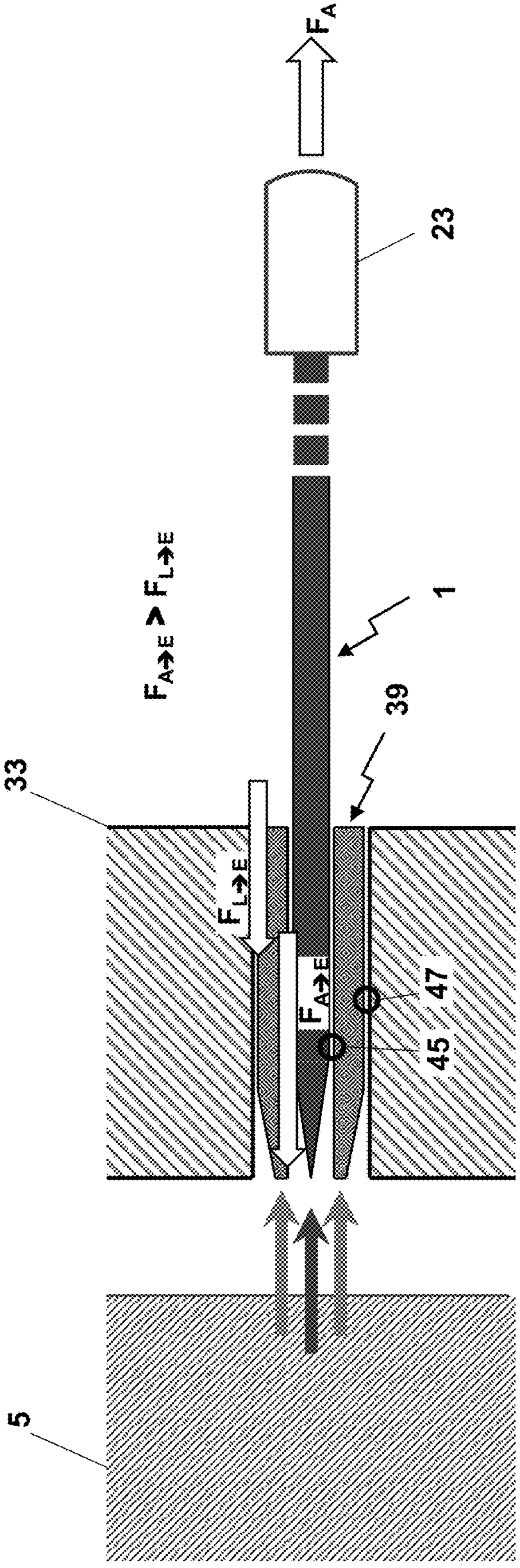
FIG. 16 is a schematic longitudinal sectional view of an exemplary embodiment of the light applicator during extraction from the positioning element, wherein the protective sleeve has just assumed the first axial position with respect to the insertion portion, but is still in the axial desired position with respect to the positioning element.

In FIG. 16, the needle tip 9 is maximally retracted proximalwards into the protective sleeve 39 so that the protective sleeve 39 again has the protecting first axial position with respect to the insertion portion 1. The first interface 45 can have a stop which, at the maximum proximal position of the insertion portion 1, strikes proximalwards with respect to the protective sleeve 39, so that the distal resistance force $F_{A \to E}$ is greater than the distal resistance force $F_{L \to E}$ generated by the engaged second interface 47. The operator must increase the proximal pull-out force $F_A$ to overcome the distal resistance force $F_{L \to E}$ and release the second interface 47 from its engagement. The protective sleeve 39 then leaves its desired position in the receptacle 35 proximalwards and remains in the first axial position with respect to the insertion portion 1.

Figure 17:
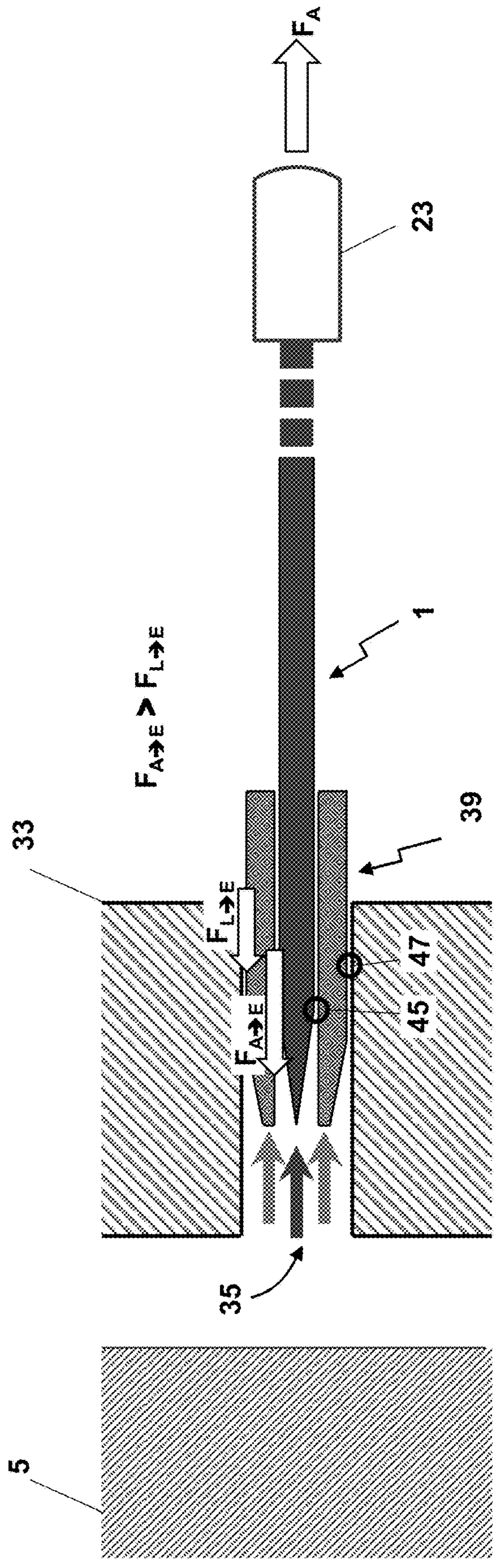
FIG. 17 is a schematic longitudinal sectional view of an exemplary embodiment of the light applicator when pulled out of the positioning element with the protective sleeve in the first axial position with respect to the insertion portion and after the protective sleeve has left the axial desired position in the positioning element proximalwards.

As soon as the engagement of the second interface 47 is released, as shown in FIG. 17, the pull-out force $F_A$ is counteracted by a lower sliding friction force $F_{L \to E}$ of the second interface 47, so that the protective sleeve 39, which is in the protecting first axial position with respect to the insertion portion 1, can simply be pulled proximalwards out of the receptacle 35. The needle tip 9 remains protected by the protective sleeve 39 located in the first axial position. Likewise, the protective sleeve 39 protects the operator and/or patient from accidental pricking with the needle tip 9.

Figure 18:
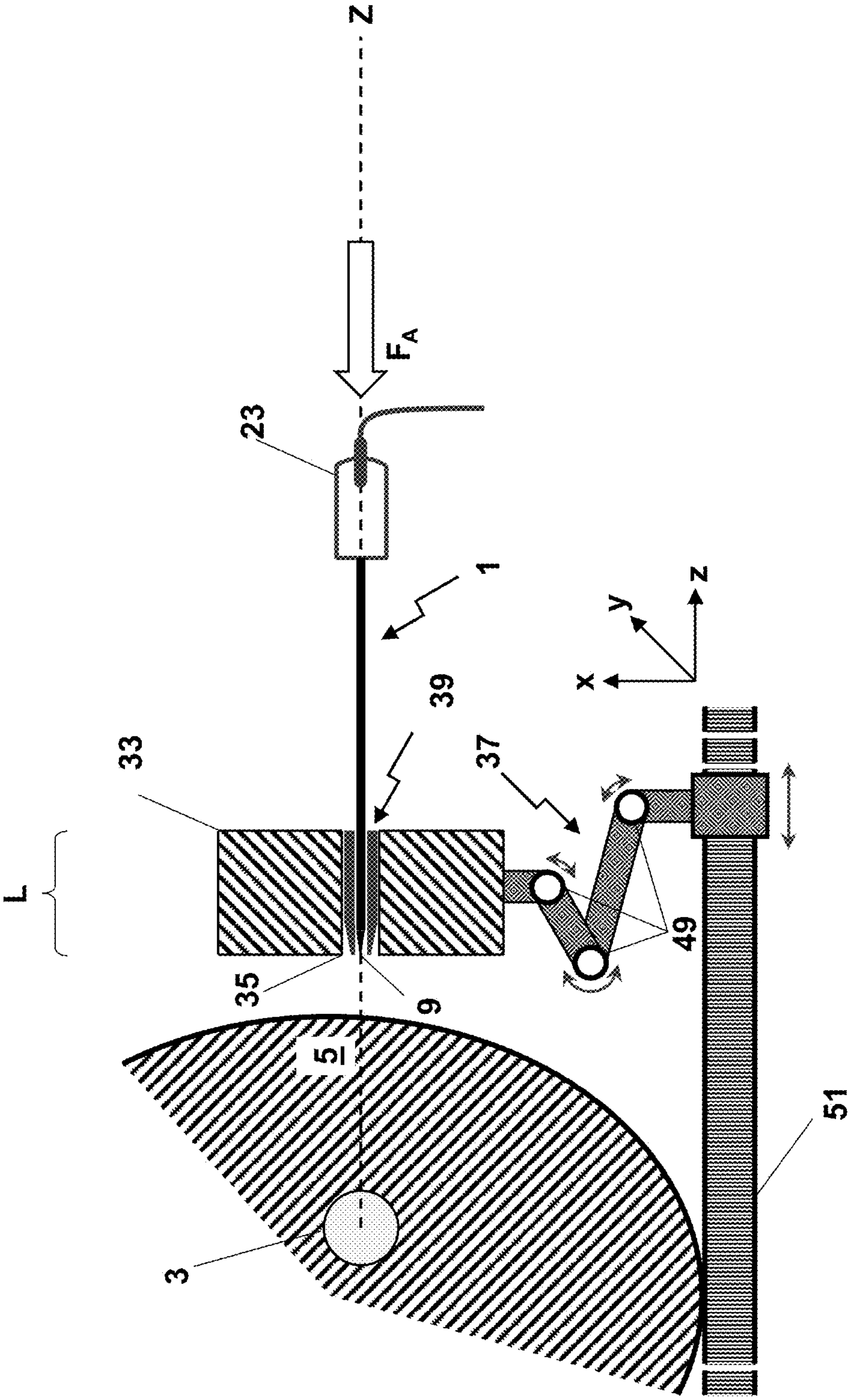
FIG. 18 is a schematic longitudinal sectional view of an exemplary embodiment of a light applicator system disclosed herein to explain the fixation of the positioning element relative to the patient's body.

FIG. 18 shows the fixing of the positioning element 33 relative to the patient's body 5 in greater detail. The fixing element 37 here has an articulated arm with several joints 49, wherein the positioning element 33 can be fixed in preferably six degrees of freedom, i.e. positioned as desired in three spatial directions x,y,z and oriented as desired in three angular settings. A treatment table 51 serves here as a local reference body with respect to which the positioning element 33 can be positioned and fixed in orientation. The patient's body 5 is preferably also fixed on the treatment table 51 and/or assumes a fixed position on or against it. The positioning element 33 can rest with a distal side on the skin 5*a* of the body 5. Preferably, the positioning element 33 is even glued to the skin 5*a*.

The positioning element 33 can be a perforated plastics plate, in the form of a perforated plate or a perforated grid. In order to be able to guide the orientation of the protective sleeve 39 in a defined manner, it is advantageous if the receptacle 35 extends over a certain length L in the Z direction. For this purpose, the positioning element 33 can have a corresponding thickness L. Alternatively, each receptacle 35 can have a sleeve extension extending in the proximal Z-direction, which is fixedly or detachably connected to the positioning element 33, so as not to make the positioning element 33 unnecessarily massive and heavy. However, a massive and heavy design of the positioning element 33 can also be advantageous for certain applications.

In FIGS. 19 to 26, the operating principle of the interfaces 45, 47 is explained in greater detail using an exemplary embodiment. In the exemplary embodiment shown, the interfaces 45, 47 each have one or more elastically deformable engagement elements 53, 55, here in the form of O-rings. A first engagement element 53 of the first interface 45 is seated between the insertion portion 1 and the protective sleeve 39 with a radially outer part in a radially circumferential first groove 57 arranged on the inside of the protective sleeve 39. A radially inner part of the first engagement element 53, which is smaller here than the radially outer part, lies, in the first axial position of the protective sleeve 39 shown in FIG. 19, in a radially circumferential first counter groove 59 arranged externally on the insertion portion 1. A second engagement element 55 of the second interface 47 is seated between the protective sleeve 39 and the positioning element 33 with a radially inner part in a radially circumferential second groove 61 arranged externally on the protective sleeve 39. A radially outer part of the second engagement element 55, which is smaller here than the radially inner part, lies in the maximum distal position, i.e. desired position, of the protective sleeve 39, shown in FIGS. 21 to 25, with respect to the receptacle 35 in a radially circumferential second counter groove 63 arranged on the inside of the receptacle 35 of the positioning element 33. As soon as the engagement elements 53, 55 are in the respective counter grooves 59, 63, the corresponding interfaces 45, 47 are "engaged", i.e. the corresponding resistance force $F_{L\rightarrow E}$ Or $F_{A\rightarrow E}$ is temporarily increased.

Figure 19:
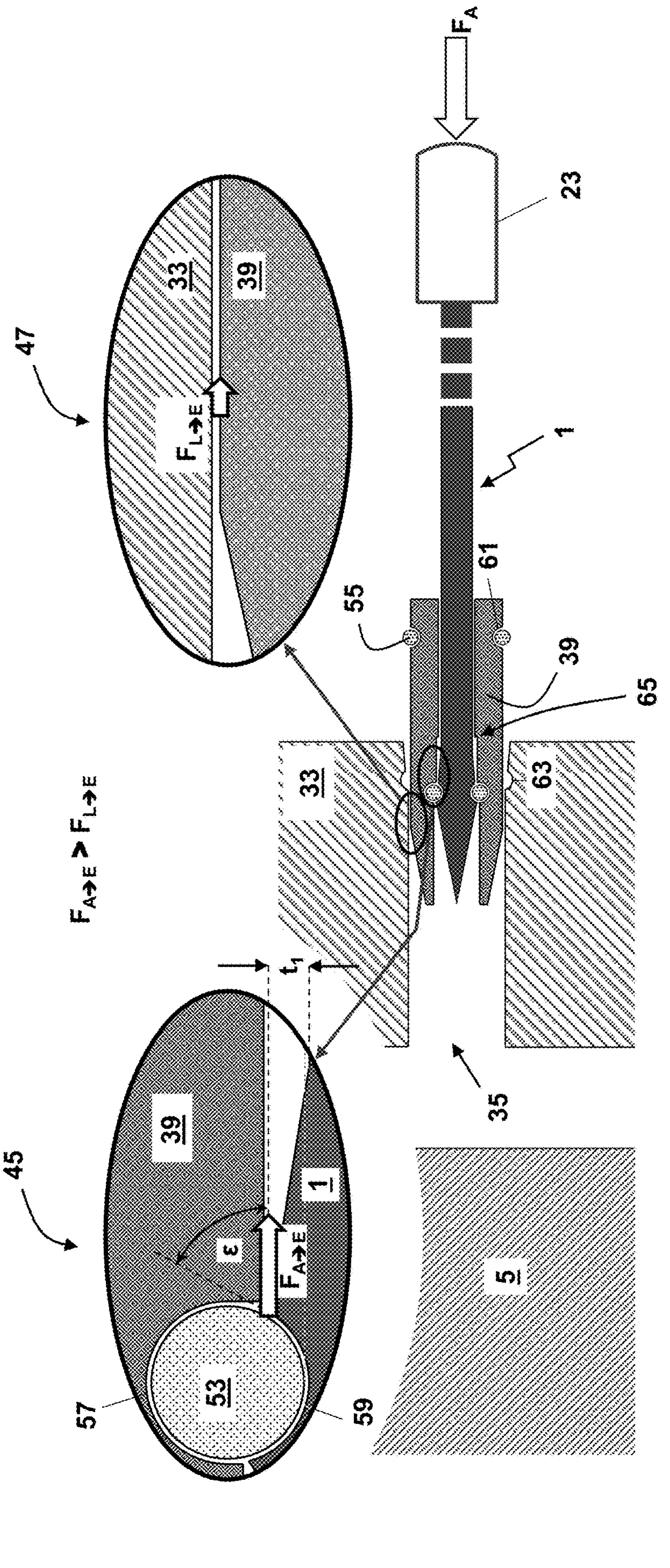
FIG. 19, FIG. 20, FIG. 21, FIG. 22, FIG. 23, FIG. 24, FIG. 25, and FIG. 26 are schematic longitudinal sectional views showing details of an exemplary embodiment of a light applicator system disclosed herein analogous to FIGS. 11 to 17 in various positions of the light applicator.

When the protective sleeve 39 is inserted into the receptacle 35, as shown in FIG. 19, the first engagement element 53 is engaged in the counter groove 59 and the second engagement element 55 is engaged outside the second counter groove 63. Therefore, the proximal resistance force $F_{A\rightarrow E}$ of the first interface 45 is higher than the proximal resistance force $F_{L\rightarrow E}$ of the second interface 47, which results only from the sliding frictional force between the protective sleeve 39 and the receptacle 35. Therefore, only the part of the piercing force $F_A$ that corresponds to the sliding friction force between the protective sleeve 39 and receptacle 35 acts distalwards on the engaged first engagement element 53. However, this force component is not sufficient to compress the first engagement element 53 radially outwards to such an extent that the counter groove 59 disengages distally. The proximal-side radial penetration depth $t_1$ of the first engagement element 53 into the first counter groove 59 is accordingly selected in such a way that a certain minimum distal force must be exerted by the insertion portion 1 on the first engagement element 53 in order to compress it radially outwards to such an extent that the counter groove 59 disengages distalwards. Below this minimum force, the insertion portion 1 is secured distally in the protective sleeve 39 located in the first axial position. Distalwards, the protective sleeve 39 is captively secured to the insertion portion 1 by the latter engaging behind an inner stop 65 of the protective sleeve 39 by means of a projection, a protrusion or a thickening. Alternatively or additionally, the counter groove 59 is designed asymmetrically in such a way that the counter groove 59 can only disengage distalwards, but not proximalwards, from the first engagement element 53.

The resistance force $F_{A\rightarrow E}$ of the first interface 45 depends not only on the proximal radial penetration depth $t_1$ of the first engagement element 53 into the first counter groove 59, but also on the geometry of the first engagement element 53 as well as the geometry of the first counter groove 59. Here, the engagement elements 53, 55 are designed as O-rings and the cross-sectional geometry of the counter grooves 59, 63 is circular-arc-shaped with a corresponding diameter to accommodate the respective O-ring 53, 55 with an accurate fit. The resistance force $F_{A\rightarrow E}$ of the first interface 45 also depends on a ramp angle ε shown in FIG. 19, which can be between 0° and 90°, wherein the resistance force is $F_{A\rightarrow E}$ is maximum for 90° and minimum for 0°. The ramp angle ε is accordingly selected so that a certain minimum distal force must be exerted by the insertion portion 1 on the first engagement element 53 in order to compress the latter radially outwards to such an extent that the counter groove 59 is released distalwards.

Figure 20:
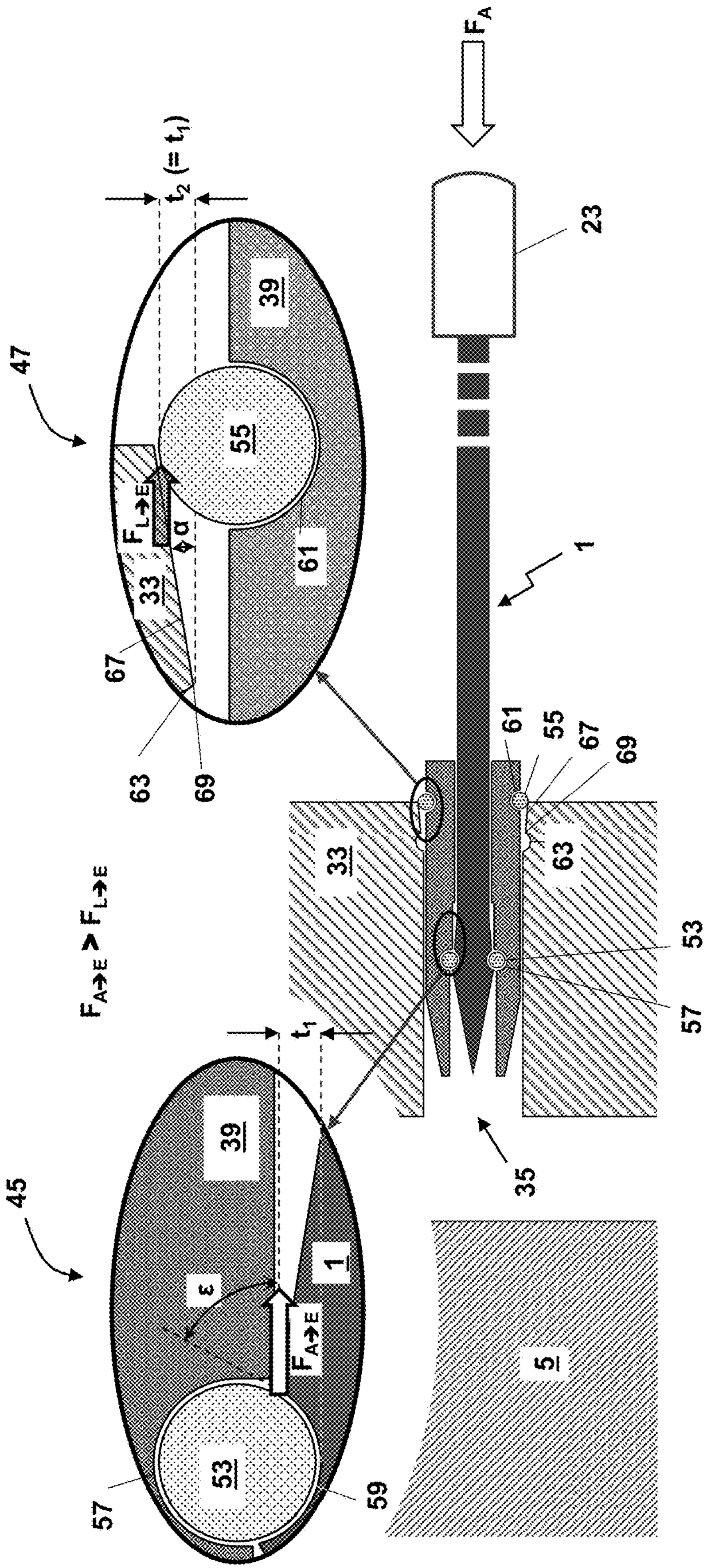

In FIG. 20, the protective sleeve 39 is inserted so far distalwards into the receptacle 35 that the second engagement element 55 just abuts the positioning element 33. The first interface 45 with the first engagement element 53 is unchanged from FIG. 19. The proximal end of the receptacle 35 widens proximalwards and thus forms a tapered ramp surface 67. This, in conjunction with the tapered outer diameter of the protective sleeve 39 at the distal end of the protective sleeve, not only facilitates insertion of the protective sleeve 39 into the receptacle 35, but the ramp surface 67 also serves to compress the second engagement element 55 radially inwards. In this way, the proximal resistance force $F_{L\rightarrow E}$ of the second of the second interface 47 is held in a defined manner below the proximal resistance force $F_{A\rightarrow E}$ of the first interface 45.

A proximal end 69 of the second counter groove 63, which here is also a distal end of the ramp surface 67, determines a proximal-side radial penetration depth $t_2$, by which the second engagement element 55 must be compressed radially inwards before it can expand outwards again into the counter groove 63, i.e. engages there. If the O-rings 53, 55 have the same cross-section and are made of the same material, the amount $t_2$ can correspond to the amount $t_1$ of the first interface 45. However, so that the first interface 45 does not become detached when the second engagement element 55 is compressed, i.e. the first engagement element 53 is compressed, a ramp angle α of the ramp surface 67 is selected to be shallower than the ramp angle ε of the first interface 45, i.e. $\alpha<\varepsilon$. This ensures that the resistance force $F_{A\rightarrow E}$ of the first interface 45 is greater than the resistance force $F_{L\rightarrow E}$ of the second interface 47 until the protective sleeve 39 has reached the maximum distal position, i.e. the desired position, in the receptacle 35 and the second engagement element 55 has engaged in the second counter groove 63.

Figure 21:
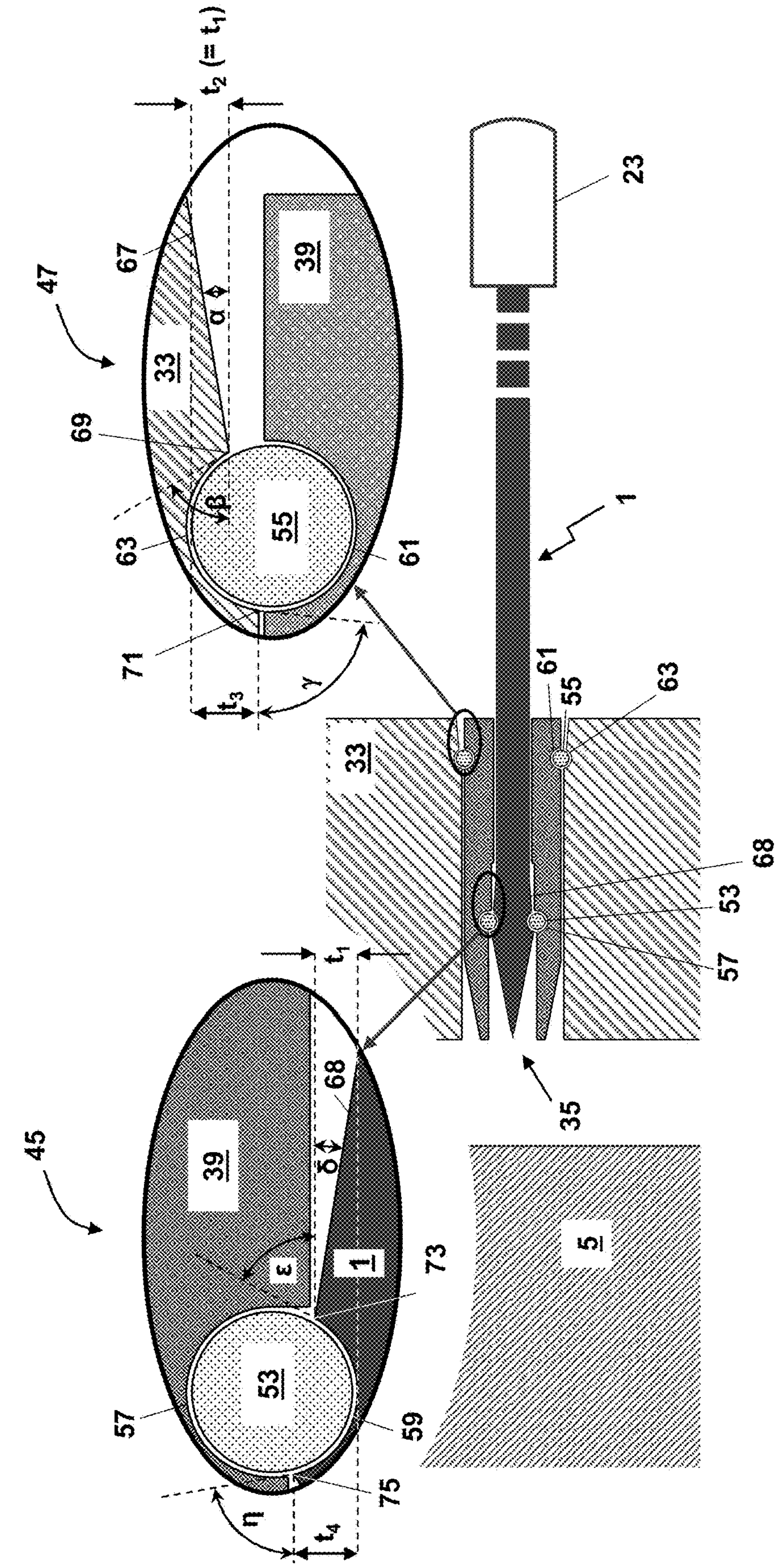

FIG. 21 shows both interfaces 45, 47 in an engaged state. The protective sleeve 39 is in the first axial position with respect to the insertion portion 1 as well as in the maximum distal position in the receptacle 35, i.e. in the desired position, since the first interface 45 is engaged in the first counter groove 59 by means of the first engagement element 53 and the second interface 47 is engaged in the second counter groove 63 by means of the second engagement element 55. The counter grooves 59, 63 are each designed asymmetrically in such a way that the respective resistance forces $F_{A\rightarrow E}$ and $F_{L\rightarrow E}$ when leaving the engaged position differ from each other in the distal direction and in the proximal direction.

The second interface 47 may, for example, form a stop in that a distal end 71 of the second counter groove 63 extends radially inwards sufficiently to provide a distal-side radial depth of penetration $t_3$ of the second engagement element 55 into the second counter groove 63, wherein $t_3>t_2$. The second engagement element 55 may be such that it cannot in fact be compressed by the penetration depth $t_3$ or this would only be possible with an improperly high application of force. In addition, the second counter groove 63 defines a relatively steep distal-side ramp angle γ wherein $\gamma>\varepsilon$. Thus, the second engagement element 55 in the second counter groove 63 forms a distal stop which determines the maximum distal position, i.e. the desired position, of the protective sleeve 39 in the receptacle 35.

The first interface 45 is inversely asymmetrical in an analogous manner. The proximal-side radial penetration depth $t_1$ of the first engagement element 53 into the first counter groove 59 is determined by a proximal end 73 of the first counter groove 59. A distal-side radial penetration depth $t_4$ of the first engagement element 53 into the first counter groove 59 is determined by a distal end 75 of the first counter groove 59, wherein $t_4>t_1$. The amounts $t_1$, $t_2$, $t_3$ and $t_4$ may be chosen such that $t_4=t_3>t_2=t_1$. In this respect, the first engagement element 53 may be such that it cannot in fact be compressed by the penetration depth $t_4$ or this would only be possible with an improperly high application of force. In addition, the first counter groove 59 defines a relatively steep distal-side ramp angle η, wherein $\eta>\varepsilon$. Thus, the first engagement element 53 forms a proximal stop in the first counter groove 59 and captively secures the protective sleeve 39 to the insertion portion 1. The insertion portion 1 also forms a ramp surface 68 on the outside, analogous to the ramp surface 67 of the second interface 47. The ramp surface 68 extends from the first counter groove 59 proximalwards, so that the insertion portion 1 tapers proximalwards with a ramp angle δ, which may be equal to the ramp angle α, over a certain distance by approximately the amount $t_1$. The ramp angle δ is chosen to be so shallow that the resistance force $F_{A\rightarrow E}$ of the first interface 45 when the needle tip 9 is retracted into the protective sleeve 39 is smaller than the resistance force $F_{L\rightarrow E}$ of the engaged second interface 47 and thus the first interface 45 engages before the second interface 47 disengages and the protective sleeve 39 leaves the desired position proximalwards.

Figure 22:
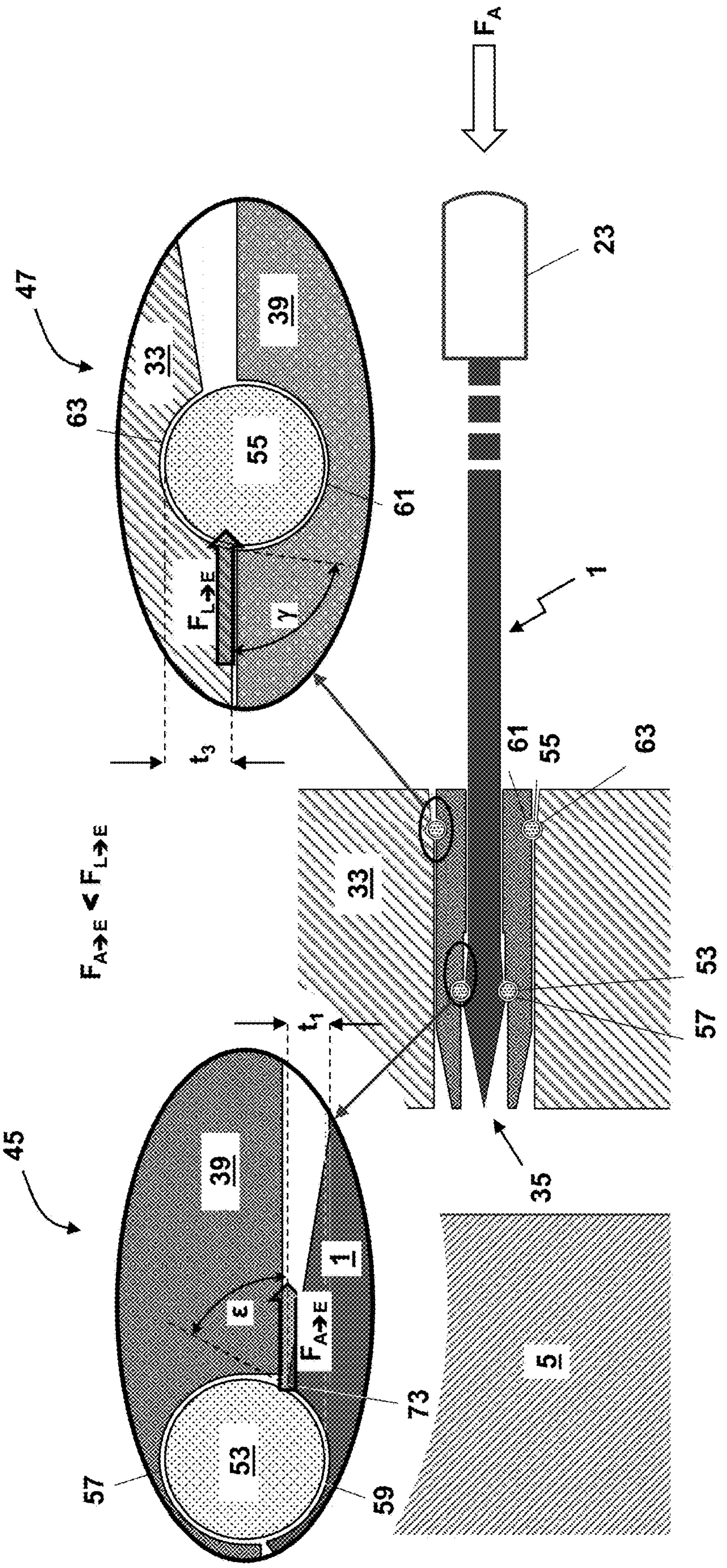

FIG. 22 shows the resulting resistance forces $F_{A\rightarrow E}$ and $F_{L\rightarrow E}$ when a distal piercing force $F_A$ is applied to the handle element 23 in the engaged position of FIG. 21. The proximal resistance force $F_{L\rightarrow E}$ of the second interface 47 is now higher than the proximal resistance force $F_{A\rightarrow E}$ of the first interface 45 (because $t_3>t_1$ and $\gamma>\varepsilon$). As a result, the first counter groove 59 presses with a proximal-side ramp surface with the ramp angle ε against the engaged first engagement element 53, so that the proximal end 73 of the first counter groove 59 presses distalwards past the first engagement element 53, with elastic deformation of the latter.

Figure 23:
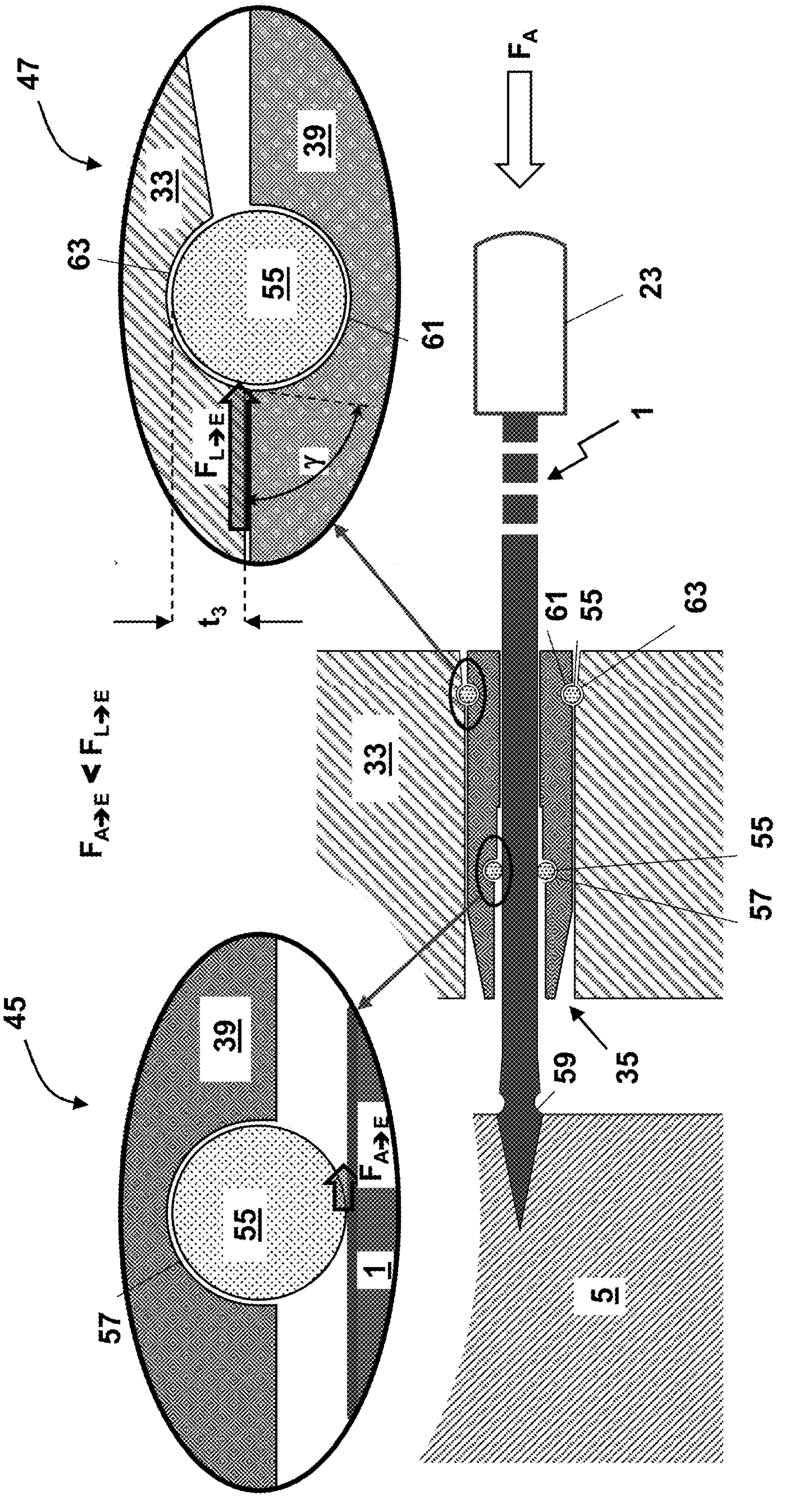

In FIG. 23, the proximal end 73 of the first counter groove 59 is pushed distally past the first engagement element 53 with elastic deformation of the latter and thus overcomes the initially higher resistance force $F_{A\rightarrow E}$ of the first interface 45. The protective sleeve 39 remains in the maximum distal position with respect to the receptacle 35, but has left the first axial position with respect to the insertion portion 1 as a result of the insertion portion 1 being pressed further distalwards. Now only a relatively low sliding friction force forms the resistance force $F_{A\rightarrow E}$ of the first interface 45, so that the insertion portion 1 can be relatively easily pierced into the body 5.

Figure 24:
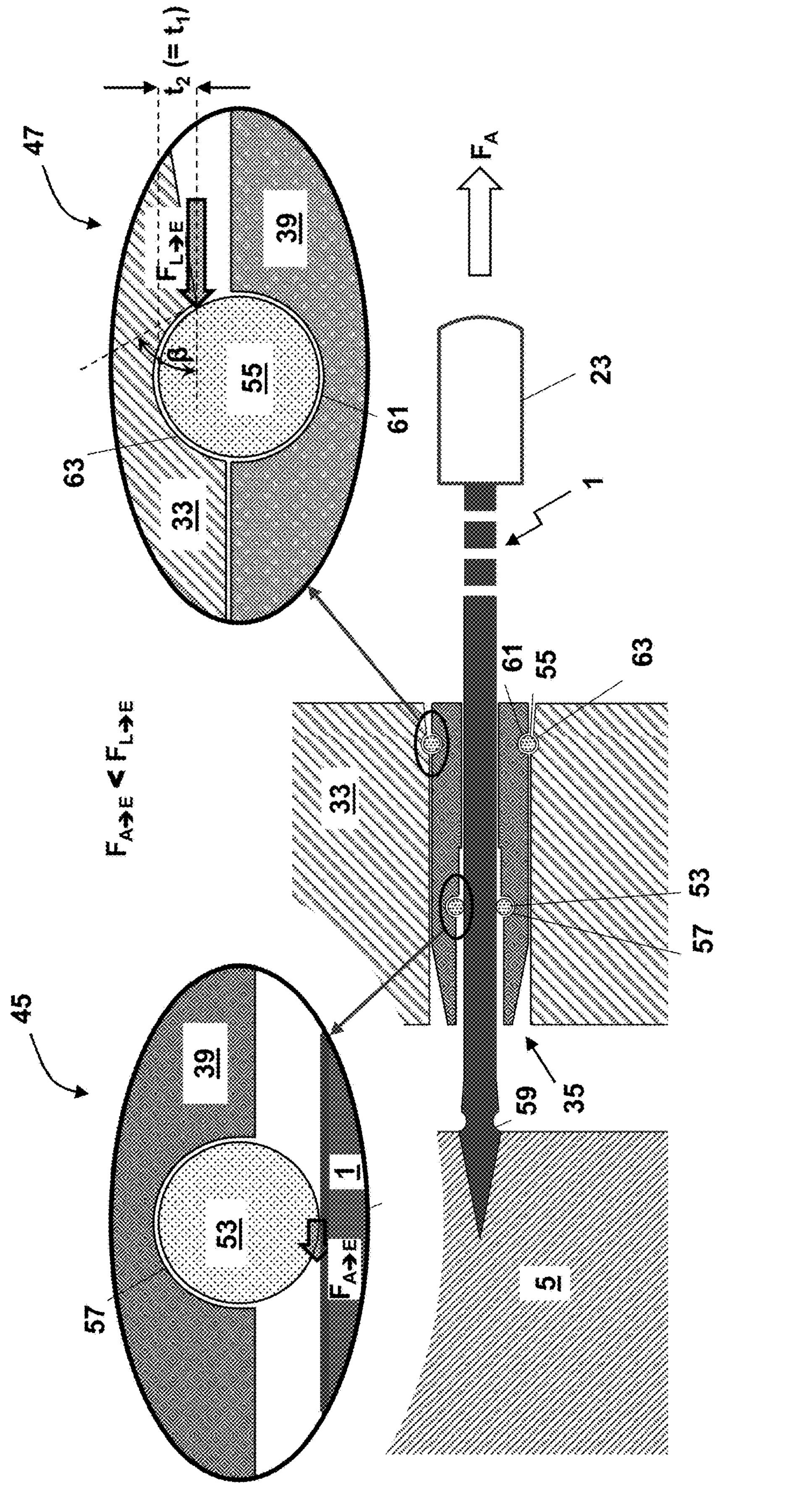

In FIG. 24, the insertion portion 1 is pulled out of the body 5 with a proximal pull-out force $F_A$. As in FIG. 23, the sliding frictional force, which forms the resistance force $F_{A\rightarrow E}$ of the first interface 45 is less than the resistance force $F_{L\rightarrow E}$ of the second interface 47. The resistance force $F_{L\rightarrow E}$ of the second interface 47 is determined on the one hand by the proximal-side penetration depth $t_2$ of the second engagement element 55 into the second counter groove 63 and on the other hand by a proximal-side ramp angle β of the second counter groove 63. The ramp angle β of the second interface 47 can correspond to the ramp angle ε of the first interface 47. Thus, the protective sleeve 39 remains in the maximum distal position, i.e. the desired position, in the receptacle 35, wherein the needle tip 9 is drawn proximally into the protective sleeve 39.

Figure 25:
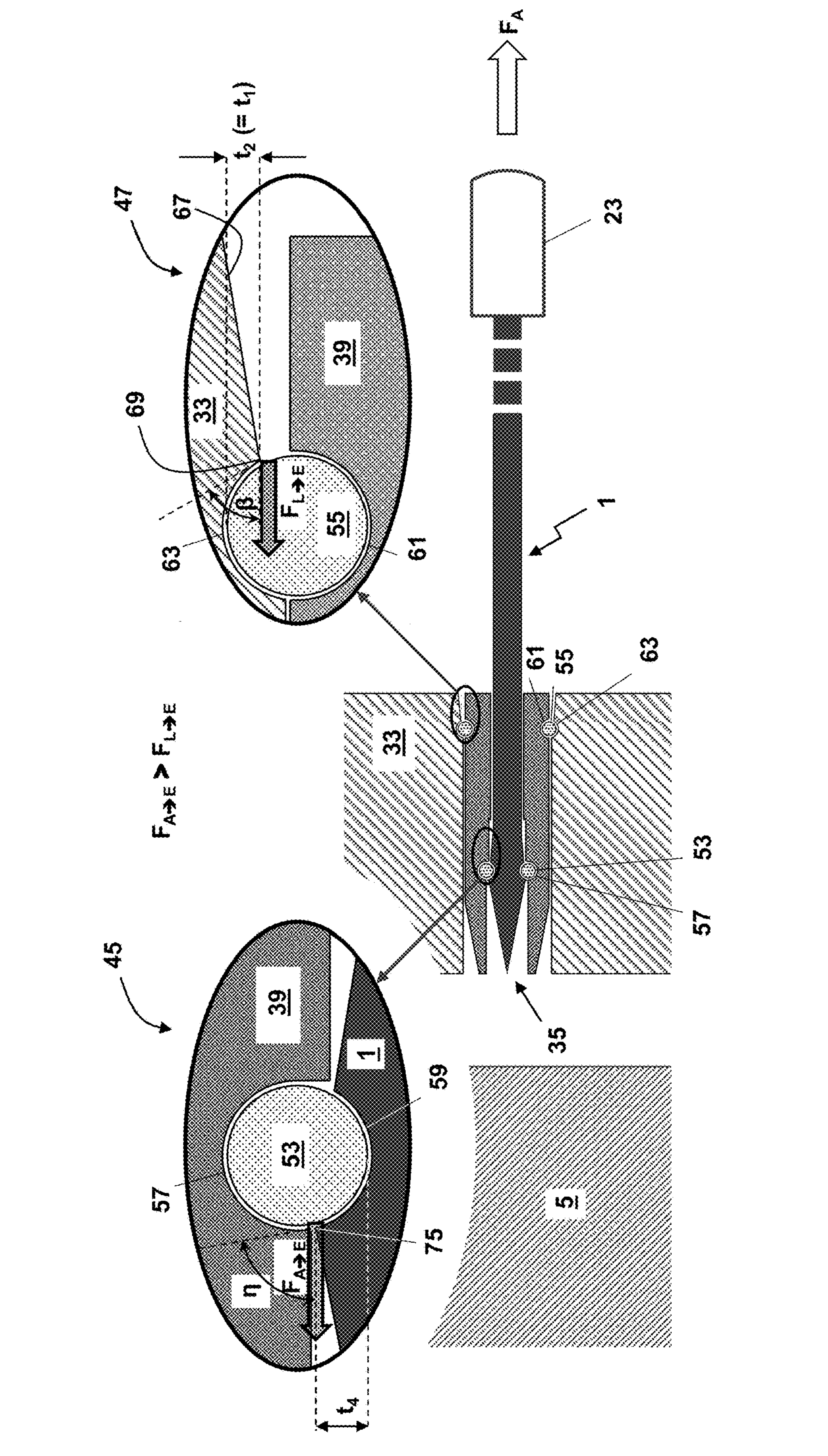

In FIG. 25, the first interface 45 is engaged again so that the protective sleeve 39 is in the first axial position with respect to the insertion portion 1, in which it grips the needle tip 9 protectively. Due to the relatively high penetration depth $t_4$ and the relatively steep ramp angle η, which together form a de facto proximal stop for the insertion portion 1, the distal resistance force $F_{A\rightarrow E}$ of the first interface 45 is greater than the distal resistance force $F_{L\rightarrow E}$ of the second interface 47 (because $t_4>t_2$ and $\eta>\beta$). As a result, the second counter groove 63 compresses the second engagement element 55 with the proximal-side ramp angle β so that it is pressed proximalwards past the proximal end 69 of the second counter groove 63 until the second interface 47 is disengaged and the protective sleeve 39 leaves the desired position proximalwards.

Figure 26:
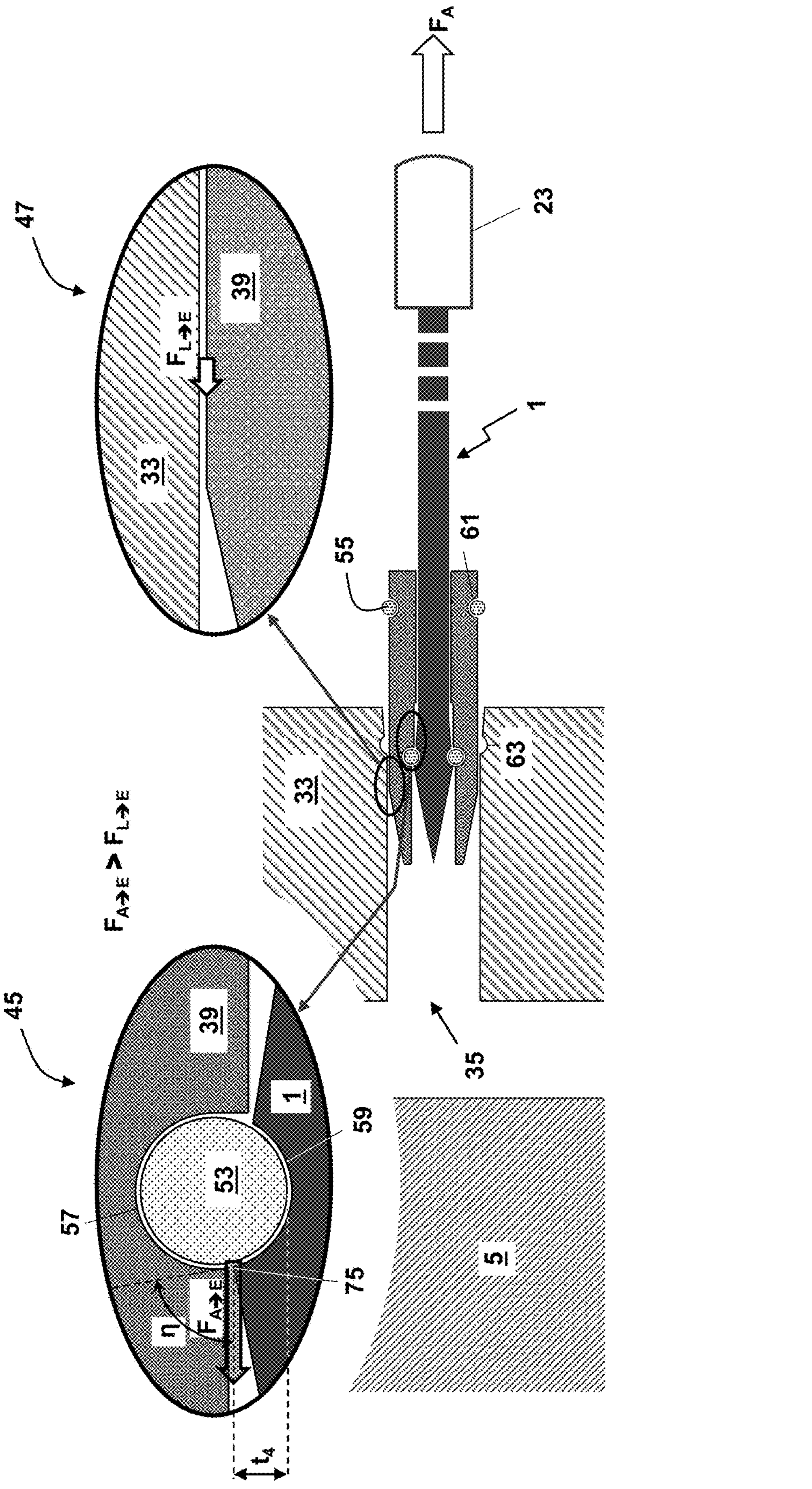

In FIG. 26, the second interface 47 is fully disengaged and the protective sleeve 39 is pulled out of the receptacle 35 in the first axial position proximalwards with the first interface 45 engaged. The resistance force $F_{L\rightarrow E}$ of the second interface 47, which in this case is only generated by a sliding frictional force, is significantly lower than the resistance force $F_{A\rightarrow E}$ of the first interface 45, since the relatively high penetration depth $t_4$ and the relatively steep ramp angle η of the first counter groove 59 together effectively form a distal stop for the protective sleeve 39.

Figure 27:
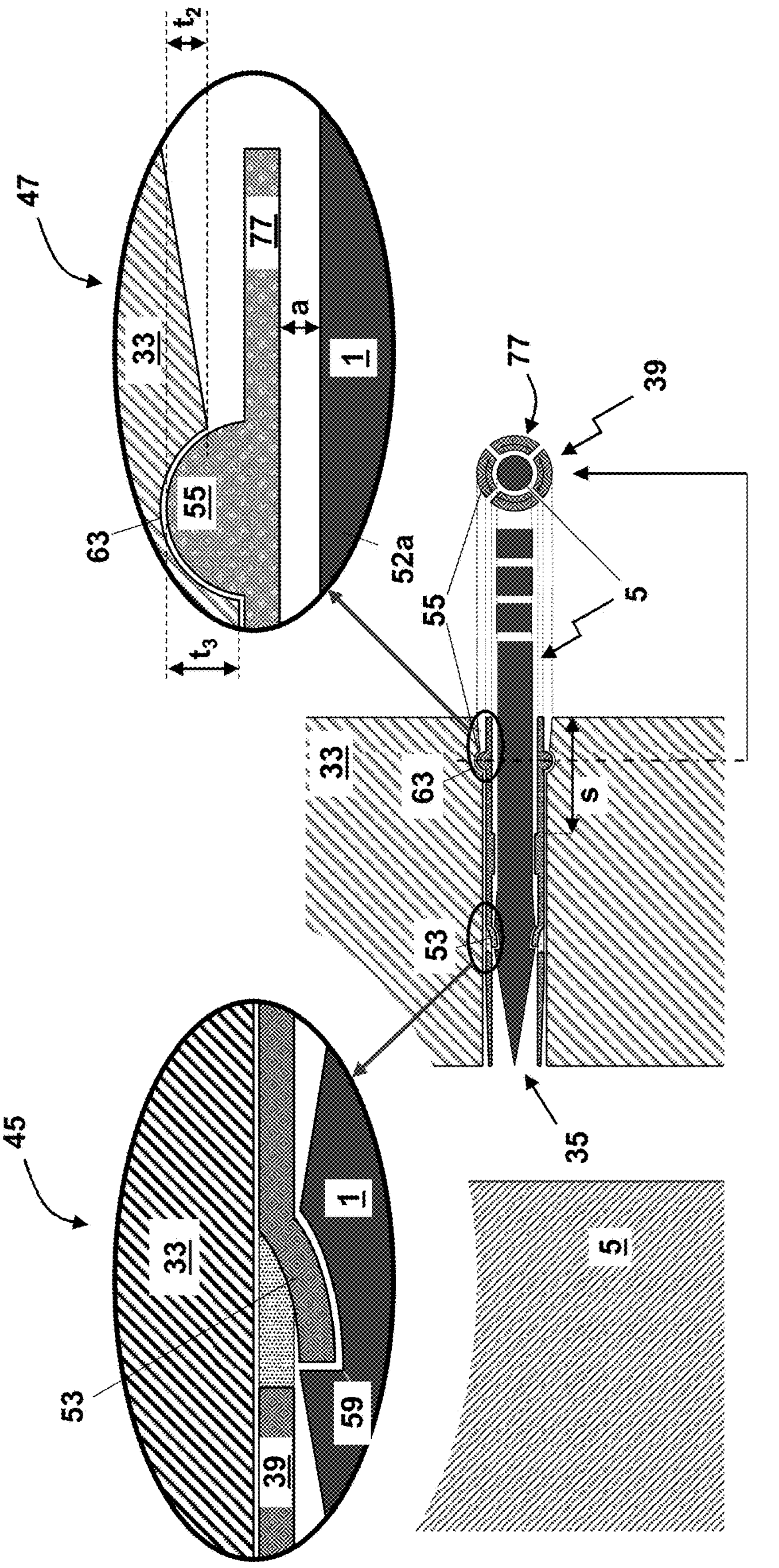
FIG. 27 is a schematic longitudinal sectional view of an alternative exemplary embodiment of a light applicator system disclosed herein.

FIG. 27 shows an alternative embodiment in which the engagement elements 53, 55 are an integral part of the protective sleeve 39. In other exemplary embodiments, it would also be conceivable that the first engagement element 53 is an integral part of the insertion portion 1 and/or the second engagement element 55 is an integral part of the positioning element 33. In this case, the first engagement element 53 of the first interface 45 is formed by at least one spring tongue arranged on the inner side of the protective sleeve 39, which can engage or latch into a corresponding indentation 59 on the outer side of the insertion portion 1. Preferably, the first engagement element 53 is formed by two or more spring tongues that are evenly distributed circumferentially. The at least one spring tongue 53 is hinged on the proximal side and forms a relatively flat proximal-side ramp angle, so that the protective sleeve 39 can be moved proximalwards from the first axial position with respect to the insertion portion 1 and the spring tongue 53 yields radially outwards in the process. Distally, the spring tongue 53 forms a stop which abuts against a steep distal-side flank of the recess 59 when the protective sleeve 39 is pushed distalwards into the first axial position shown. As a result, the protective sleeve 39 is captively secured to the insertion portion 1.

The second engagement element 55 could be formed by one or more outwardly directed spring tongues, analogously to the first engagement element 53. In the exemplary embodiment according to FIG. 27, however, the second engagement element 55 is formed by a radial projection which extends outwards from an outer side of the protective sleeve 39 and engages in a second recess 63, which here corresponds to the second counter groove 63 according to the exemplary embodiment shown in FIGS. 19 to 26. Here, the protective sleeve 39 is slotted over a length s in a proximal end region, wherein protective sleeve end portions 77 are created, which have a radial distance a from the insertion portion 1 and can thus be elastically bent inwards. This allows the engagement element 55 arranged on the protective sleeve end portions 77 to be pressed elastically inwards when the second interface 47 is engaged and disengaged. The radial distance a is selected here such that it is greater than or equal to the proximal-side penetration depth $t_2$ of the second engagement element 55 into the second recess 63, but less than the distal-side penetration depth $t_3$ of the second engagement element 55 into the second recess 63, i.e. $t_3>a>t_2$ applies. The engagement elements 53, 55 may themselves be elastically deformable, but need not be. The engagement elements 53, 55 can be designed here to be merely movable.

The numbered designations of the components or directions of movement as “first”, “second”, “third”, etc. are chosen herein purely arbitrarily to distinguish the components or directions of movement from one another and can be chosen arbitrarily differently. This does not imply any order of importance. A designation of a component or technical feature as “first” should not be misunderstood to mean that there must be a second component or technical feature of this type. Furthermore, any method steps can be carried out in any order and/or partially or completely overlapping in time, unless explicitly explained otherwise or imperatively required.

Equivalent embodiments of the parameters, components or functions described herein that would appear obvious to a person skilled in the art in light of this description are intended to be included herein as if they had been explicitly described. Accordingly, the scope of the claims is intended to encompass such equivalent embodiments. Any "can" features designated as optional, advantageous, preferred, desirable or similar are to be understood as optional and not as limiting the scope of protection.

The described embodiments are to be understood as illustrative examples and do not constitute an exhaustive list of possible embodiments. Any feature disclosed in the context of an embodiment may be used alone or in combination with one or more other features, regardless of the embodiment in which the features were described in each case. While at least one exemplary embodiment is described and shown herein, variations and alternative embodiments that would appear obvious to a person skilled in the art in view of this description are included within the scope of protection of this disclosure. Moreover, the term "have" herein is not intended to exclude additional other features or process steps, nor is "one" or "a" intended to exclude a plurality.

While specific embodiments of the invention have been shown and described in detail to illustrate the application of the principles of the invention, it will be understood that the invention may be embodied otherwise without departing from such principles.

LIST OF REFERENCE CHARACTERS

1 insertion portion
3 tissue to be examined/treated
5 organic body
**5*a*** skin of the organic body
7 actively light-emitting element/LED
**7*a*** end face of the LED
9 needle tip
**9*a*** sleeve-shaped portion of the needle tip
11 conductor element
13 connection point
15 lateral force application $F_{L,S}$
17 laterally acting external body
19 detachment force
21 light applicator
23 handle element
25 connection cable
27 hand of an operator
29 lateral force $F_{L,H}$
31 light applicator system
33 positioning element
35 receptacle
37 fixing element
39 protective sleeve
43 light of the LED
45 first interface
47 second interface
49 joints
51 treatment table
53 first engagement element
55 second engagement element
57 first groove
59 first counter groove/indentation
61 second groove
63 second counter groove/indentation
65 stop
67, 68 ramp surfaces
69 proximal end of the second counter-groove/indentation
71 distal end of the second counter groove/indentation
73 proximal end of the first counter groove/indentation
75 distal end of the first counter groove/indentation
77 protective sleeve end portions
$d_1$ length of the insertion portion without needle tip
$d_2$ length of the needle tip
$Z_N$ longitudinal axis of the insertion portion
Z desired piercing direction
$F_A$ manual piercing or pull-out force
L axial length of the receptacle
$t_1$ proximal-side penetration depth of the first engagement element
$t_2$ proximal-side penetration depth of the second engagement element
$t_3$ distal-side penetration depth of the second engagement element
$t_4$ distal-side penetration depth of the first engagement element
a radial distance
s length of the protective sleeve end portions
α, β, γ, ε, η, δ ramp angle
$F_{A \rightarrow E}$ resistance force of the first interface
$F_{L \rightarrow E}$ resistance force of the second interface

The invention claimed is:

1. A light applicator system for examination and/or treatment of an organic body, the light applicator system comprising:
- at least one light applicator;
- a positioning element; and
- an elastically deformable and/or movable engagement element,
- wherein the light applicator comprises a distal-side insertion portion with at least one actively light-emitting element at the distal end for piercing tissue of the organic body,
- wherein the insertion portion comprises a needle tip arranged at least partially distally of the at least one actively light-emitting element and tapering distalwards,
- wherein the positioning element is fixable at least temporarily in a defined position and orientation relative to the organic body and has at least one receptacle for the at least one light applicator, in which the at least one light applicator has, at least temporarily, a defined orientation relative to the organic body,
- wherein the light applicator further comprises a protective sleeve which is axially movable relative to the insertion portion and which in a first axial position relative to the insertion portion protectively surrounds the needle tip and in a second axial position, determined by an axial position of the insertion portion relative to the positioning element, is pushed back relative to the insertion portion proximalwards from the needle tip,
- wherein the protective sleeve serves as an insertion sleeve into the at least one receptacle of the positioning element,
- wherein the engagement element is arranged between the insertion portion and the protective sleeve such that the engagement element elastically yields or moves upon overcoming an axial force to such an extent that the protective sleeve can reach the first axial position distalwards and/or can leave the first axial position proximalwards, and wherein the engagement element is a first of at least two elastically deformable and/or movable engagement elements with a second engagement element and the axial force is a first axial force of at least two axial forces with a second axial force, wherein the second engagement element is arranged between the protective sleeve and the at least one receptacle of the positioning element such that, upon overcoming the second axial force, the second engagement element elastically yields or moves to such an extent that the protective sleeve can reach the desired position in the positioning element distalwards and/or leave the desired position in the positioning element proximalwards.

2. The light applicator system according to claim 1, wherein the protective sleeve has, at least in portions, an outer diameter that fits accurately into an inner diameter of the at least one receptacle of the positioning element.

3. The light applicator system according to claim 2, wherein the outer diameter of the protective sleeve tapers distalwards at the distal end and/or the inner diameter of the at least one receptacle of the positioning element expands proximalwards at the proximal end.

4. The light applicator system according to claim 1, wherein the insertion portion of the light applicator is rigid and has a greater length in an axial direction than the protective sleeve.

5. The light applicator system according to claim 1, wherein the protective sleeve is captively secured to the insertion portion of the light applicator.

6. The light applicator system according to claim 1, wherein the light applicator comprises, on a proximal side, a handle element for manual positioning of the light applicator.

7. The light applicator system according to claim 6, wherein the axial position of the insertion portion relative to the positioning element is manually adjustable by positioning the handle element in an axial direction.

8. The light applicator system according to claim 1, wherein the protective sleeve is secured in the first axial position during a distalwards insertion of the light applicator into the at least one receptacle of the positioning element until the protective sleeve reaches a desired position in the positioning element in the at least one receptacle of the positioning element, in which the insertion portion can be pushed distalwards out of the protective sleeve.

9. The light applicator system according to claim 8, wherein the protective sleeve is secured in the desired position in the positioning element when the light applicator is pulled out proximally from the at least one receptacle of the positioning element until the protective sleeve assumes the first axial position with respect to the insertion portion, in which the protective sleeve can be pulled out proximally from the at least one receptacle of the positioning element.

10. The light applicator system according to claim 1, wherein the engagement element is part of the protective sleeve and/or the insertion portion.

11. The light applicator system according to claim 1, wherein the second engagement element is part of the protective sleeve and/or the positioning element.

12. The light applicator system according to claim 1, wherein distalwards the first axial force is greater than the second axial force and proximalwards the second axial force is greater than the first axial force.

13. The light applicator system according to claim 1, wherein the first engagement element is part of the protective sleeve and/or the insertion portion.

14. The light applicator system according to claim 13, wherein the second engagement element is part of the protective sleeve and/or the positioning element.

15. The light applicator system according to claim 14, wherein distalwards the first axial force is greater than the second axial force and proximalwards the second axial force is greater than the first axial force.

* * * * *